US011089996B2

(12) United States Patent
Sitton et al.

(10) Patent No.: US 11,089,996 B2
(45) Date of Patent: Aug. 17, 2021

(54) SYSTEM AND METHOD FOR THE OBJECTIVE EVALUATION OF SYMPATHETIC NERVE DYSFUNCTION

(71) Applicant: Episcan Global, LLC, Tulsa, OK (US)

(72) Inventors: David Michael Sitton, Broken Arrow, OK (US); Christopher P. Dougherty, Rogers, AR (US); Samuel F. Arndt, III, Tulsa, OK (US)

(73) Assignee: Episcan Global, LLC, Tulsa, OK (US)

( * ) Notice: Subject to any disclaimer, the term of this patent is extended or adjusted under 35 U.S.C. 154(b) by 0 days.

(21) Appl. No.: 15/842,091

(22) Filed: Dec. 14, 2017

(65) Prior Publication Data

US 2018/0289317 A1 Oct. 11, 2018

Related U.S. Application Data

(60) Provisional application No. 62/434,169, filed on Dec. 14, 2016.

(51) Int. Cl.
*A61B 5/00* (2006.01)
*A61B 5/053* (2021.01)
(Continued)

(52) U.S. Cl.
CPC ........... *A61B 5/4824* (2013.01); *A61B 5/053* (2013.01); *A61B 5/4041* (2013.01); *G16H 10/40* (2018.01); *G16H 10/60* (2018.01); *G16H 15/00* (2018.01); *G16H 20/10* (2018.01); *G16H 20/30* (2018.01); *G16H 20/40* (2018.01); *G16H 50/70* (2018.01);
(Continued)

(58) Field of Classification Search
None
See application file for complete search history.

(56) References Cited

U.S. PATENT DOCUMENTS 3,533,397 A 10/1970 Scher
4,697,599 A 10/1987 Woodley et al.
(Continued)

OTHER PUBLICATIONS

Epi-Scan P100. Datasheet [online], Epi-Scan, Mar. 7, 2017. Retrieved from internet: URL: ,https://d3ciwvs59ifrt8.cloudfront.net/3bd68e1c-690a-4ba9-83c2-28ddd1 c46f5c/f3141771-b21c-40ce-81f6-ef4fde3b9bbb.pdf> (Year: 2017).*
(Continued)

*Primary Examiner* — Erica S Lee
(74) *Attorney, Agent, or Firm* — Smith Patent, LLC; Chalin A. Smith

(57) ABSTRACT

Various methods and machines have been used in the past to measure electrical characteristics of living tissue for purpose of locating an area of abnormal nervous system activity. However, whereas prior art methodologies merely allow for the detection of pain, the apparatus, system and method of the present invention allow for the objective assessment pain severity that finds utility not only the initial diagnosis but also the on-going treatment of any disease, disorder or injury associated therewith. To that end, the apparatus, system and method of the present invention allows medical practitioners to non-invasively and quantitatively distinguish organic pain from psychosomatic pain and legitimate pain patients from drug seekers and opiod addicts, as well as to directly and objectively compare the efficacy of different drug regimens and therapy protocols.

21 Claims, 20 Drawing Sheets

(51) Int. Cl.
*G16H 15/00* (2018.01)
*G16H 10/60* (2018.01)
*G16H 10/40* (2018.01)
*G16H 50/70* (2018.01)
*G16H 20/40* (2018.01)
*G16H 20/10* (2018.01)
*G16H 20/30* (2018.01)
*A61B 5/01* (2006.01)
*A61B 5/145* (2006.01)
*A61B 8/08* (2006.01)
*A61B 5/1455* (2006.01)

(52) U.S. Cl.
CPC .............. *A61B 5/0022* (2013.01); *A61B 5/01* (2013.01); *A61B 5/14532* (2013.01); *A61B 5/14546* (2013.01); *A61B 5/14551* (2013.01); *A61B 5/4266* (2013.01); *A61B 8/08* (2013.01); *A61B 2503/40* (2013.01); *A61B 2560/0214* (2013.01)

(56) References Cited

U.S. PATENT DOCUMENTS

| | | | |
|---|---|---|---|
| 5,897,505 A | 4/1999 | Feinberg et al. | |
| 7,826,900 B2 | 11/2010 | Stellar et al. | |
| 7,991,462 B2 | 8/2011 | Storm | |
| 8,774,893 B2 * | 7/2014 | Wilder-Smith | A61B 5/01 600/382 |
| 9,630,011 B2 | 4/2017 | Lipari | |
| 9,782,122 B1 | 10/2017 | Pulliam et al. | |
| 2005/0049474 A1 | 3/2005 | Kellogg et al. | |
| 2005/0119701 A1 | 6/2005 | Lauter et al. | |
| 2014/0159912 A1* | 6/2014 | Fraden | A61B 5/002 340/870.02 |
| 2014/0276188 A1 | 9/2014 | Jardin | |
| 2014/0378859 A1 | 12/2014 | Taratorin et al. | |
| 2016/0007878 A1 | 1/2016 | Leuthardt et al. | |
| 2016/0302720 A1 | 10/2016 | John et al. | |
| 2017/0143256 A1 | 5/2017 | Navani | |
| 2017/0165485 A1* | 6/2017 | Sullivan | A61N 1/36021 |

OTHER PUBLICATIONS

David R. Longmire, MD, "An Electrophysiological Approach to the Evaluation of Regional Sympathetic Dysfunction: A Proposed Classification", Pain Physician, 2006, 9:69-82.

* cited by examiner

COLUMNS

|  | C1 | C2 | C3 | C4 | C5 | C6 |
|---|---|---|---|---|---|---|
| R1 | R1C1 (16) | R1C2 (13) | R1C3 (10) | R1C4 (1) | R1C5 (4) | R1C6 (7) |
| R2 | R2C1 (17) | R2C2 (14) | R2C3 (11) | R2C4 (2) | R2C5 (5) | R2C6 (8) |
| R3 | R3C1 (18) | R3C2 (15) | R3C3 (12) | R3C4 (3) | R3C5 (6) | R3C6 (9) |
| R4 | R4C1 (34) | R4C2 (31) | R4C3 (28) | R4C4 (19) | R4C5 (22) | R4C6 (25) |
| R5 | R5C1 (35) | R5C2 (32) | R5C3 (29) | R5C4 (20) | R5C5 (23) | R5C6 (26) |
| R6 | R6C1 (36) | R6C2 (33) | R6C3 (30) | R6C4 (21) | R6C5 (24) | R6C6 (27) |

ROWS

For example: R2C2 is reading of location Row 2, Column 2.
R6C3 is reading of location Row 6, Column 3

THE EPI-SCAN IS PROGRAMMED TO TAKE THE MEASUREMENTS IN THE SEQUENCE SHOWN. THIS IS FOR ALL STANDARD MONTAGES.

FIG. 11

SYSTEM AND METHOD FOR THE OBJECTIVE EVALUATION OF SYMPATHETIC NERVE DYSFUNCTION

PRIORITY

This application claims the benefit of U.S. Provisional Application Ser. No. 62/434,169 filed Dec. 14, 2016, the contents of which are hereby incorporated by reference in their entirety.

TECHNICAL FIELD OF THE INVENTION

The present invention relates generally to the correlation between electrical tissue parameters, such as skin conductance, with sympathetic and parasympathetic nerve function (and dysfunction). More particularly, the present invention relates to an apparatus, system and method for the non-invasive sudomotor assessment of corporeal pain that allows for the objective measurement of pain severity that, in turn, finds utility not only in the diagnosis and treatment of any underlying disorder, disease or injury associated with the measured pain levels but also in determining the appropriate drug and dosage regimen, in distinguishing organic pain from psychosomatic pain and legitimate pain patients from drug seekers and opiod addicts, and in directly and objectively comparing the efficacy of different therapy protocols and drug regimen.

BACKGROUND OF THE INVENTION

During the latter portion of the twentieth century, researchers made significant contributions to the measurement of perspiration and its relationship to the sympathetic portions of the human nervous system. It is accepted that moist skin is associated with the ability to conduct electricity more readily than dry skin, the former having a lower resistance to electrical flow. When the nerve supply to the skin is interrupted, skin moisture drops, conductance falls, and the skin resistance level rises.

Early investigations of the variability of skin electrical responses created by changing parameters of stimulation indicated that the measurement of conductance levels, not responses, would provide more stable results. This removed the need for any external or internal stimulation and thus created an improvement in methodology.

Although this technology was originally intended for the measurement of human skin conductance, such electrical assessment has also been used for other types of deep tissue, e.g. in the fields of marine biology and plant physiology. Therefore the term Selective Tissue Conductance (STC) was adopted as being more appropriate for the broad range of biological materials that could be evaluated with this technology.

There are also two other methodological differences that separate Selective Tissue Conductance technology from other forms of skin conductance measurement, namely Spatial Selectivity and Temporal Selectivity.

Early methods of measuring skin conductance or resistance often consisted of passing an electrical test current between a static reference electrode and a roving or exploring electrode which was moved over the areas of the skin to be assessed. If it happened that the reference and roving electrodes were placed on opposite sides of the body, then the electrical flow would transverse the body creating transcorporeal currents. If this path flowed through electrically sensitive organs, e.g. the heart, theoretical if not actual risks of arrhythmia would be increased.

In U.S. Pat. No. 4,697,599, the details of which are hereby incorporated by reference, Woodley et al. discloses a selective tissue conductance meter that overcomes the problem of spatial selectivity by using a fixed, bipolar concentric electrode that is simply pressed against the skin surface. The concentric electrode disclosed in the '599 patent consists of a center contacting electrode and an outer ring electrode which surrounds the center electrode. Additionally, a circular gap filled with an electrical insulating material is provided between the center electrode and the outer ring electrode. Consequently, when the concentric electrode is pressed against the skin and an electrical test current is discharged from the center electrode, the path of the electrical test current is restricted so that the test current travels from the center contact electrode to the outer ring electrode by volume conduction through only the superficial layers of the skin, thus preventing the possibility of producing a trans-corporeal current.

More specifically, the device disclosed in the '599 patent is a diagnostic device capable of measuring the conductance of human or animal tissue which includes a housing capable of being held in one hand by the user of the device and a concentric electrode mounted on the exterior of the housing. An electric circuit is located in the housing and is connected to the concentric electrode for producing an electrical signal having a pulse frequency that varies directly according to the conductance of the human or animal tissue placed in contact with the electrode. The electric circuit includes a voltage to frequency converter having an oscillator with logarithmic output so that the pulse frequency varies logarithmically according to the conductance measured by the electrodes. The logarithmic output permits a wide range of tissue conductance to be measured. A source of low voltage power is connected to the circuit and a detector is provided for detecting the electrical signal to permit the user to know the pulse frequency of the signal.

Almost ten years later, in U.S. Pat. No. 5,897,505, Feinberg et al. describe an improvement on the Woodley construction, wherein the selective tissue conductance apparatus is modified to include a thermography sensor. However, while the prior art enables identification of the presence of pain in one or more certain locations, it fails to enable the automated measurement and objective assessment of the degree of the pain and thus the severity of the underlying injury, disease or disorder. Thus, there is a need in the art and the present invention aims for an apparatus, system, and method for the objective evaluation of corporeal pain.

SUMMARY OF THE INVENTION

A primary goal of the present invention is to provide an apparatus, system and method that allows for the objective evaluation and assessment of patient/subject pain, which, in turn, can be used to identify and characterize the underlying injury, disease or disorder and determine an appropriate therapy, including the adjustment, addition or elimination of chemical, electrical, or physical therapeutic devices Illustrative aspects and embodiments of the present invention in accordance with the foregoing objective are as follows:

One objective of the present invention is to provide a hand-held, low-voltage, cost effective diagnostic device for measuring selective tissue conductance, and optionally other physiological parameters, for the sympathetic sudomotor assessment of corporeal pain that addresses one or more art-recognized problems and/or drawbacks of prior art alternatives. To that end, in the context of the present invention, the diagnostic device is generally characterized by a sensor head and associated device housing, wherein the sensor head includes, at a minimum, a pair of spaced electrodes (i.e., a bipolar electrode assembly) that may be applied to the skin to measure and quantify the level of conductance therein, and the device housing contains the requisite power and circuitry components to enable activation of the one or more sensor head components and transduction of their respective signals to an output that may be correlated to pain, abnormal sensation, or sympathetic nerve dysfunction.

Prior art instruments that utilize a fixed electrode require the user to use great care in accurately placing the instrument against the patient's skin to assure proper uniform contact. This requires that the instrument always be perpendicular to the surface of the skin. Consequently, if not aligned properly, the instrument will provide an erroneous reading. Moreover, ensuring that the instrument is properly aligned when placing the electrode on parts of the body that are curved or contoured, or in places difficult to reach, is particularly problematic. Thus, to address alignment problems present in certain prior art alternatives, it is an object of the present invention to provide the hand-held, low-voltage diagnostic device of the present invention with an optional flexible coupling connecting sensor head to device housing. In preferred embodiments, this coupling may take the form of an articulated, pivoting base for mounting the sensor head to the device housing. For example, the device may include a ball-and-socket type coupling that allows the base of the sensor head to pivot and/or rotate freely to assure proper uniform tissue contact. In one preferred embodiment, the base is provided with a curved or ball type surface that is pivotably received in a mating socket provided on the distal neck portion of the device housing. In an alternate preferred embodiment, the coupling components are reversed. In either case, the free pivoting movement causes the sensor head to automatically move into a properly aligned perpendicular orientation when placed against the skin.

Prior art instruments that utilize permanently installed sensor heads can be problematic as, during use, the permanent electrode can become contaminated with skin oils, moisture, or other contaminates that case errors in the skin conductance measurements. In addition, some clinical procedures require cleaning and disinfecting of the electrodes prior to use on the patient. Cleaning and disinfecting using normal aqueous or alcohol base solutions add additional surface conductivity unless the electrode is properly dried to remove the residual moisture (which also can cause erroneous measurements). Accordingly, to address the drawbacks of the permanently installed sensor head, it is an object of the present invention to manufacture the sensor head as a replaceable, detachable biopolar electrode assembly of sufficiently low cost that may be used either as an interchangeable electrode (allowing for proper sterilization and drying). Alternatively, the sensor head may be manufactured as a disposable product.

In certain embodiments of the present invention, the sensor head can be readily and securely attached to (and detached from) the device housing with each procedure and/or test subject, for example via a screw-in type mounting with spring loaded contact pins to complete the measurement circuit. Alternatively, the present invention contemplates a sensor head that can be physically separated from the device housing, thereby allowing it to be worn by a test subject over a period of time and configured for single and/or continuous monitoring and measurement. In this latter embodiment, the sensor is optionally provided with means to record measurements, such as an integral or on-board memory chip or memory card, and/or means to transmit recorded measurements to the hand-held housing, or, alternatively, directly to a local or remote computer system, database or physician. It may further be optionally configured to directly or indirectly coordinate with or connect to one or more preset ports on a standard laptop computer, smartphone, or tablet.

Many selective tissue conductance meters of the prior art use a direct (DC) current method wherein a small DC voltage is applied between the outer ring and center core of the concentric bipolar electrode assembly. As noted above, the amount of current measured between the two parts of the electrode is proportional to the skin conductivity. However, a problem with the DC current method is that, as the DC potential is applied to the skin or other body tissue, an ionophoresis effect is produced in which the current flow between the electrodes increases over time, thus producing progressively increased measurement values based upon the duration of the application of the DC currently. Consequently, in the context of DC-based measurements, controlling the time interval is critical for obtaining consistent results. However, the present invention eliminates this problem in certain preferred embodiments by utilizing alternating current (AC), more particularly a high frequency (1 to 100 kHz) AC signal to measure the current between the respective components of the bipolar electrode assembly. This eliminates the ionophoresis effect caused by the use of a DC current. Accordingly, in the context of the present invention, time of measurement is not a critical variable and thus measurements obtained are more consistent and accurate.

One objective of the present invention is to provide a multifunctional diagnostic device in which the sensor head is outfitted with multiple sensors for measuring multiple physiological parameters. For example, in one preferred embodiment, the sensor head and/or device housing optionally include other sensors such as (a) thermography cameras and optical infrared scanners to assess the heat and temperature of the affected region; (b) sweat-based glucose, lactate and theophylline biosensors that enable non-invasive transdermal scoring of analyte concentration in tissue, particularly muscle tissue; (c) pulse-oximeters to allows for measurement of oxygen saturation levels and assess pre- and post-flow to the affected region; (d) ultrasonic sensors and transducers that allow a medical practitioner to assess viability and recovery of muscle tissue.

In certain embodiments, the device housing may outfitted with liquid crystal display and optionally an onboard microprocessor and/or memory card or other storage means to allow for collected data to be temporarily stored, or recalled/displayed, until it can be downloaded (or uploaded) to a remote system. Alternatively, the connection between diagnostic device and associated microprocessor device can be wireless, using either short-range signal (such as a Bluetooth® or LAN network) or a long-range digital or cellular network to transfer data, thereby allowing the computer and the treating physician to be either local or remote. The onboard, local or remote microprocessor can record, transcribe and/or analyze specific measurements and/or enable local or remote analysis and diagnosis.

As noted above, in certain embodiments, the device housing can be "smart", i.e., outfitted with a programmable computer chip or other complex microprocessing components that enables on-board programming and analysis. Alternatively, the device may be a simplified "dummy"

device that receives all its programming instructions from a remote microprocessor, such as a laptop computer, tablet or Smartphone. So as to reduce user error, in a preferred embodiment, the device housing is outfitted with a display screen that allows the user to cycle through a menu of pre-programmed operating modes and modules, more preferably options that walk the medical practitioner through the requisite set-up, initialization, measurements and/or recordation processes.

In certain preferred embodiment, the components of the diagnostic device may be powered by a pre-charged power source, such as one or more AA or 9-volt batteries. In an alternate embodiment, the diagnostic device can utilize a rechargeable power source, for example, a rechargeable lithium-ion battery, and optionally coupled with requisite charging accessories such as a charging cord, adapter and/or charging cradle.

It is yet another objective of the present invention to provide a kit for measuring selective tissue conductance, and optionally other physiological parameters, for the sympathetic sudomotor assessment of corporeal pain that includes a diagnostic device as described above coupled with:
- one or more pre-powered or rechargeable batteries and associated charging accessories;
- one of more audio output devices such as wired or wireless earphones, headphones, and/or external speakers;
- one or more disposable sensor heads;
- one or more memory cards or memory chips for locally storing data on the diagnostic device;
- one or more cables for connecting the diagnostic device of the present invention to microprocessing device such as a laptop computer, a tablet, smartphone, or external hard drive;
- requisite analysis and/or report-writing software to facilitate subject evaluation; and/or
- written instructions to ensure proper operation.

Yet another objective of the present invention is to provide a series of pre-programmed montages to automate measurement intake for specific injuries and/or tissue types and ensure consistency. For example, the montage may comprise a grid or pattern of vertical and horizontal lines that form four adjacent quadrants of equal size, each of which includes an equal number of aligned measurement sites that are mirrored in adjacent horizontal, vertical and diagonal quadrants so as to enable ready comparison.

In one aspect, the present invention provides an apparatus, system and method that allows for the measurement, recording and analysis of skin conductance measurements to evaluating for sensory nerve pain testing and dysfunction, as well as degree of pain. As noted above, in the context of the present invention, readings at particular locations are compared to normative or baseline measurements. The degree to which a particular reading exceeds an associated "normal" reading determines not just the presence of pain in the noted location but the degree of pain, and, by extension, the severity of the underlying injury, disease or disorder. In preferred embodiments, the present invention utilizes the above-noted pre-programmed montages to automate multiple readings within a particular region of the body. Results are then compared (a) between sides along horizontal lines and (b) between proximal and distal regions measured along vertical lines. By comparing across quadrants, the physician can identify asymmetrical reading(s) and correlate the location of such asymmetry with the degree of pain involved and thus the severity of any underlying injury, disease or disorder. In this manner, the subject acts as his or her own control.

In an alternate embodiment, asymmetrical locations may be identified by comparison to (a) a subject's current readings (e.g., by comparing to a mirrored bilateral equivalent); (b) a subject's prior readings (e.g., from a previous assessment, potentially before the onset of therapy); or (c) a normative data set of "normal" and "pain" patients, optionally further divided and characterized according to sex, age, injury, and body part involved.

It is a further objective of the present invention to provide for the creation of a database that includes a normative set of patient data and/or individualized patient data that may be used by the medical practitioner to identify the presence of a particular nerve disorder, characterize its severity and/or track progress over time. In a preferred embodiment, this database enables the comparison of a pre-injury baseline to a post-injury measurement to distinguish physical injury from psychosomatic pain. Also enabled is the comparison of pain relief afforded from different medications and/or therapies (e.g., opioid vs. non-opioid) and the correlation of raw data/sympathetic parameters to a particular diagnosis and/or therapy.

In yet another aspect, the present invention incorporates software and programming to automate two-point discrimination for assessment of nerve injury and recovery in an affected region.

These and other aspects are accomplished in the invention herein described. Further objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention.

BRIEF DESCRIPTION OF THE FIGURES

Various aspects and applications of the present invention will become apparent to the skilled artisan upon consideration of the brief description of figures and the detailed description of the present invention and its preferred embodiments that follows:

FIG. 11 depicts a typical 6×6 matrix, with 6 rows and 6 columns, common to the montage procedures of the present invention and a convention used for numbering of each of measurement sites.

DETAILED DESCRIPTION OF THE PREFERRED EMBODIMENTS

Figure 1A:
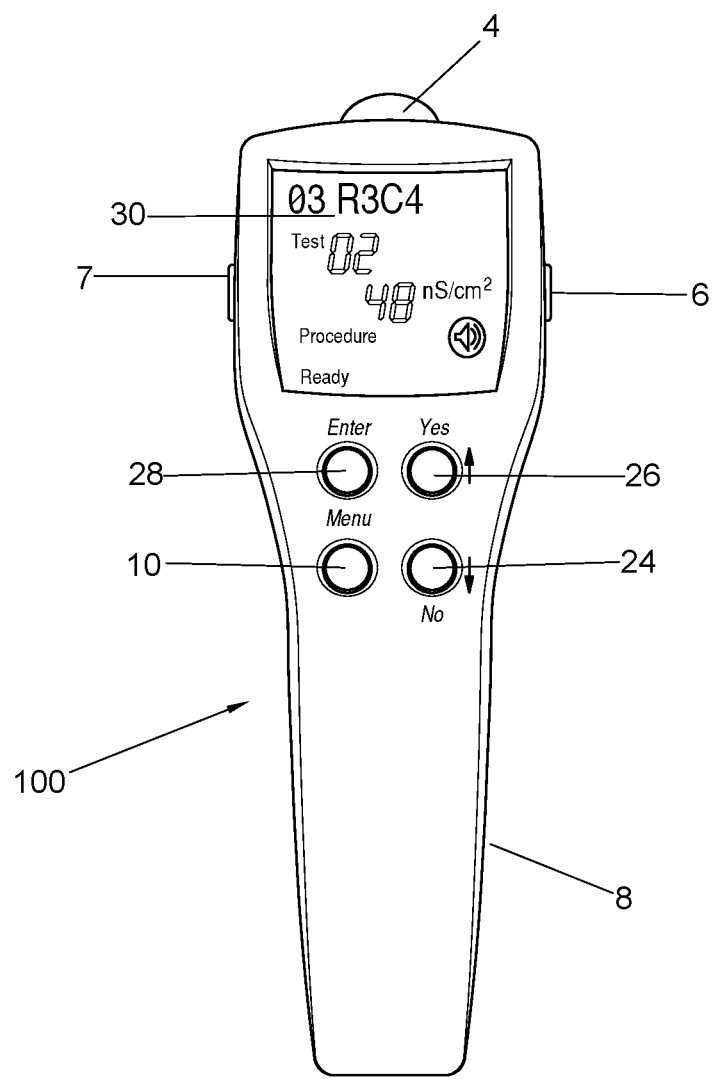
FIG. 1A is a photograph depicting a top-down view of an illustrative embodiment of a diagnostic device (100) of the present invention.

The present invention relates to new and improved handheld, low-voltage diagnostic devices for measuring selective tissue conductance, and optionally other physiological parameters, for the sympathetic sudomotor assessment of corporeal pain as well as software and hardware systems and methods associated therewith that enable the objective evaluation and assessment of patient pain, which, in turn, can be used to identify and characterize the underlying injury, disease or disorder and determine an appropriate therapy.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Unless otherwise defined, all technical and scientific terms used herein have the same meaning as commonly understood by one of ordinary skill in the art to which the present invention belongs. However, in case of conflict, the present specification, including definitions below, will control. Accordingly, in the context of the present invention, the following definitions apply:

A. Definitions:

As used herein and in the appended claims, the singular forms "a", "an" and "the" include plural reference unless the context clearly dictates otherwise. Thus, for example, reference to a "molecule" is a reference to one or more molecules and equivalents thereof known to those skilled in the art, and so forth.

The term "proximal" as used herein refers to that end or portion which is situated closest to the user of the device, farthest away from a target site on the subject's body. In the context of the present invention, the proximal end of the selective tissue conductance meter for sympathetic sudomotor assessment of the present invention includes the handle portion.

The term "distal" as used herein refers to that end or portion situated farthest away from the user of the device, closest to the a target site on the subject's body. In the context of the present invention, the distal end of the selective tissue conductance meter for sympathetic sudomotor assessment of the present invention includes the electrode head.

The terms "lengthwise" and "axial" as used interchangeably herein to refer to a direction relating to or parallel with the longitudinal axis of a device. The term "transverse" as used herein refers to a direction lying or extending across or perpendicular to the longitudinal axis of a device.

The term "lateral" pertains to the side and, as used herein, refers to motion, movement, or materials that are situated at, proceeding from, or directed to a side of a device.

The term "medial" pertains to the middle, and as used herein, refers to motion, movement or materials that are situated in the middle, in particular situated near the median plane or the midline of the device or subset component thereof.

As discussed above, the present invention relates to an apparatus, system and method for correlating electrical tissue parameters, such as skin conductance, with sympathetic and parasympathetic nerve function (and dysfunction) so as to provide a quantitative measurement for and sudomotor assessment of the presence and severity of corporeal pain. Of particular interest to the present invention is the measurement of absolute selective tissue conductance (STC) values. In the context of the present invention, the STC value corresponds to the galvanic skin response (GSR) or electrodermal response (EDR), which are known to be analogous or proportional to the expected sympathetic sudomotor activity level for the site being measured at a given time. By comparing individual (absolute) STC values to other surrounding or distant (or analogous control values), sites of STC asymmetry can be identified, assessed and characterized.

As used herein, the term "tissue" refers to biological tissues, generally defined as a collection of interconnected cells that perform a similar function within an organism. Four basic types of tissue are found in the bodies of all animals, including the human body and lower multicellular organisms such as insects, including epithelium, connective tissue, muscle tissue, and nervous tissue. These tissues make up all the organs, structures and other body contents. While the present invention is not restricted to any particular soft tissue, aspects of the present invention find particular utility in the analysis of dermal and epidermal tissues to assess nerve injury, particularly peripheral nerve damage to the neck, back, limbs and extremities. The invention also finds utility in the assessment of chronic or acute odontogenic and/or orofacial pain and the oral/dental disorders associated therewith, examples of which include, but are not limited to, pericoronitis, temporomandibular joint dysfunction (TMD), and periapical periodontitis (owing to apical infection or postendodontic therapy of high occlusal contact).

The instant invention has both human medical and veterinary applications. Accordingly, the terms "subject" and "patient" are used interchangeably herein to refer to the person or animal being treated or examined. Exemplary animals include house pets, farm animals, and zoo animals. In a preferred embodiment, the subject is a mammal, more preferably a human. In that the instant invention allows for objective characterization of subject pain, it finds particular utility in connection with non-verbal human and animal subjects, including humans suffering from autism and dementia, comatose and anesthetized subjects, patients with speaking, hearing and/or comprehension disabilities, and the like.

The human nervous system is made up two parts: the central nervous system (CNS), made up of the brain and the spinal cord, and the peripheral nervous system (PNS), which consists mainly of nerves and ganglia. The CNS integrates information it receives from, and coordinates and influences the activity of, all parts of the body. The PNS on the other hand connect the CNS to the limbs and organs, essentially serving s a relay between the brain and spinal cord and the rest of the body.

The PNS is divided in the somatic nervous system, which controls voluntary action, and the autonomic nervous system, which controls involuntary action. The autonomic nervous system (ANS) acts largely unconsciously and regulates bodily functions such as the heart rate, digestion, respiratory rate, pupillary response, urination, and sexual arousal and is the primary mechanism in control of the fight-or-flight response. Autonomic functions include control of respiration, cardiac regulation (the cardiac control center), vasomotor activity (the vasomotor center), and certain reflex actions such as coughing, sneezing, swallowing and vomiting.

The ANS has three branches: the sympathetic nervous system (SNS), the parasympathetic nervous system (PNS), and the enteric nervous system (ENS). Whereas the PNS is responsible for stimulation of "rest-and-digest" or "feed and breed" activities that occur when the body is at rest, especially after eating, the primary purpose of the SNS is to stimulate the body's "fight-or-flight" response, a term that encompasses a wide range of physical and physiological reactions to stress and injury, from accelerated heart and lung action to constriction or dilation of the blood vessels to paling or flushing or perspiration.

In the context of the present invention, electrical characteristics of living tissue are measured, assessed and correlated to sympathetic and parasympathetic nerve function (and dysfunction). Examples of such measurable electrical characteristics contemplated by the instance invention include, but are not limited to, skin conductance and skin resistance. It is well-accepted that moist skin is associated with the ability to conduct electricity more readily than dry skin, the former having a lower resistance to electrical flow. When the nerve supply to the skin is interrupted, either in the context of a physical injury or a degenerative disease condition, skin moisture drops, conductance falls, and skin resistance levels rise.

In the context of the present invention, the use of conductance as the electrical characteristic to be measured has a distinct advantage over the use of resistance because the relationship between conductance and nerve function is a direct relationship rather than an inverse relationship. As such, skin conductance measurements are easier to quantify, transduce, and correlate nerve function.

As noted above, the present invention is based on the combined principles of instrumentation and the electrophysiological effects of innervation of the sweat glands. This provides a noninvasive, painless instrument system for the quantitative measurement of selective tissue conductance", which is operationally defined herein as the relative ability of biological tissue to conduct a low voltage electrical signal, which is applied for a pre-determined period of time to a selected, limited, and restricted surface area of that tissue, and which shares those same neuroanamatomic reflex pathways as other tests of sympathetic skin activity or regional perspiration levels.

In addition to sympathetic and parasympathetic nerve function, the electrical measurements can be correlated to other physiological parameters, examples of which include but are not limited to, heme concentration, which, in turn, may be correlated to increased or decreased blood flow. Furthermore the electrical measurements can be correlated to the measurement of cell surface cytokine production as measured by the alternative embodiments of the device, e.g., in the form of an adaptable surface head.

The present invention contemplates the simultaneous measurement of other physical parameters, including, for example, temperature, pressure, oxygen saturation, glucose levels, narcotic levels, etc. Accordingly, in the context of the present invention, the testing head of the diagnostic device of the present invention may incorporate additional sensing components to allow for the measurement and recording of multiple parameters at once. Illustrative examples of such additional sensing components include, but are not limited to, thermocouples or equivalent sensors for measuring skin temperature; thermography cameras, optical infrared scanners, or ultrasonic sensors transducers for deep tissue visualization; sweat-based glucose concentration electrodes and pulse-oximeters, as well as cell surface cytokine measurement devices.

The present invention makes reference to an "electrode", more particular a "bipolar electrode assembly" for identifying local variances in skin conductance levels as an indication of sympathetically mediated or maintained pain. In the context of the present invention, the bipolar electrode assembly is comprised of a pair of concentric or otherwise aligned electrode surfaces wherein one effectively functions as the "active" electrode while the other functions as the "return". As used herein, the term "active electrode" refers to one or more conductive elements formed from any suitable metallic material, such as stainless steel, nickel, titanium, tungsten, and the like, connected, for example to a power supply and capable of generating an electric field. As used herein, the term "return electrode" refers to one or more powered conductive elements to which current flows after passing from the active electrode(s) back to the power source. This return electrode is located in close proximity to the active electrode and is likewise formed from any suitable electrically conductive material, for example a metallic material such as stainless steel, nickel, titanium, tungsten, aluminum and the like.

In order to avoid shorting, the two electrodes must be separated by a suitable non-conductive spacer fabricated from a suitable dielectric materials such as hard rubber joined to the electrodes via an epoxy.

In a preferred embodiment, the "active" and "return" components of the bipolar electrode assembly are concentrically situated and separated by an appropriate annular spacer. However, other shapes and configurations are contemplated by the present invention. Accordingly, the central contact, the annular spacer, and the outer electrode can have any shape, such as that of a circle, oval, triangle, square, rectangle or other regular, preferably closed polygon. The surface areas of the respective components can likewise vary, from smooth and planar to contoured, ridged or ribbed. However, it is preferred that the geometric centers of the respective components should be common or identical, i.e., "concentric".

In the context of the present invention, measured skin conductance parameters are compared against one or more reference points to identify areas of asymmetry. The reference point(s) for asymmetrical location identification may be provided by (a) the subject in real-time, e.g., a mirrored bilateral equivalent (e.g., left leg vs. right leg) or adjacent tissue (e.g., upper thigh vs. lower thigh); (b) a prior reading for the same subject (e.g., from a previous assessment, potentially before the onset of therapy); (c) readings from other similarly situated subjects or other positive control population; and/or (d) readings from "normal" (e.g., pain-free) subjects as negative control. The present invention refers to "normative data sets" to be used as a comparison point to identify relative high or low STC values, that are, in turn, associated with pain and/or sympathetic dysfunction. In the context of the present invention, "normative data" is data from a reference population that establishes a baseline distribution for a score or measurement, and against which the score or measurement can be compared. Normative data is typically obtained from a large, randomly selected representative sample from the wider population.

The present invention makes reference to a device housing that contains the requisite power and circuitry components to enable activation of the one or more sensor head components and transduction of their respective signals to an output that may be correlated to pain, abnormal sensation, or sympathetic nerve dysfunction. Illustrative examples of suitable circuitry are described in U.S. Pat. Nos. 4,697,599 and 5,897,505, the contents of which are hereby incorporated by reference in their entirety.

The present invention involves the collection, storage and analysis of patient data, including measured selective tissue conductance values that finds particular utility in connection with pain evaluation and assessment. In the context of the present invention, collected data is held in an electromagnetic or optical form for access by a computer processor. Illustrative examples of suitable electromagnetic and optical storage media include, but are not limited to, magnetic tape; magnetic disks; optical discs such as CDs, DVDs, and Blu-ray disks; flash memory; main memory (e.g., dynamic RAM); and cache memory. The present invention contemplates data storage at both the local level (e.g., in the device housing or sensor head itself, in a smartphone, tablet, laptop, desktop or LAN computer) and at the remote level (e.g., a cloud-based database).

Data collection occurs at the sensor head which, as noted above, may be mounted to and demounted from the device housing or, alternatively, may be a separate component, optionally including its own power source and circuitry, that can communicate with, an optionally attach to, any number of devices and systems, both local and remote. For example, the sensor head may comprise a small, single-function or multi-functional electrode that may be worn by the subject either continuously or during periodic monitoring sessions. Accordingly, the sensor head may be optionally coupled with a strap, band or other support to enable proper positioning and alignment on the body.

Measurement data collected by the sensor head may be managed and processed on local processing and interface components, such as a smartphone or tablet application or "app", or, alternatively, on a secure cloud server synchronized with to the smartphone app or other processing component (e.g., a laptop or LAN computer).

In the context of the present invention, the associated "app" should be compatible with and operational on a wide range of phone and computer-based operating systems (e.g., Mac, Windows, Apple, Android, Linux, Unix, etc.) and preferably include a simple user-interface and several key data entry and display features such as discussed in the Examples below.

The present invention contemplates two-way communication between sensor head and the hand-held device, smartphone, tablet, laptop, and/or remote server. For example, the sensor head may send raw data to the "app", which, in turn, may analyze the data and prepare and forward a report to remote server, which, in turn, may then be reviewed by remote medical practitioner who then may send instructions for a particular therapy back down to the "app". In that patient data is highly personal and sensitive, all communication is preferably encrypted prior to transmission. Encrypted data may be uploaded to the server for processing whenever a mobile broadband or secure Wi-Fi connection is available.

In the context of the present invention, the term "medical practitioner" refers to a health professional from the fields of dentistry, medicine, nursing, occupational health, and physical therapy, examples of which include, but are not limited to medical doctors, physician's assistants, registered nurses, nurse practitioners and LPNs, medical technicians, occupational therapists, and the like. However, the present invention contemplates reliance on artificial intelligence (AI), instead of or in addition to human practitioners, to act on the "cloud based" data platform for analytics, clinical, and research uses to enhance, refine, and make recommendations of therapies. Such AI systems may also be used to identify or pre-screen for future ailments based on the data driven to the platform.

The apparatus, system and method of the present invention finds utility in connection with "open-loop", "semi-closed-loop" and "closed-loop" treatment and therapeutic regimens. In the context of the present invention, "open-loop" treatment refers to a regimen in which an a priori fixed dosage (or treatment regimen) is prescribed to a patient. In contrast, "closed-loop" treatment allows for dosages to be adjusted according to results obtained by laboratory analysis. The term "semi-closed loop" refers to an intermediate process having both fixed and dynamic components. Accordingly, the present invention finds utility in connection with both open-loop/fixed protocols, e.g., wherein a particular measurement results in the recommendation of a particular pain medicine, and closed-loop/dynamic protocols, e.g., wherein hour-to-hour or day-to-day variations in certain measurements result in revisions to the prescribed therapy, ranging from a new dosage to a new class of pharmaceutical to a recommendations for physical therapy or surgical intervention.

B. Utilities of the Present Invention:

There are a number of significant real-world applications for an apparatus, system, and method that allows for the automated measurement and objective determination of not just the location but also the degree of corporeal pain, and thus the severity of the underlying injury, disease or disorder, such as presently disclosed.

For example, the methods of the present invention, wherein measured pain data is referenced, analyzed and quantified, find utility in the assessment of nerve injuries. Accordingly, the methods of the present invention may be applied to the evaluation of abdominal dysfunction in adults with diabetic autonomic mesenteric neuropathy and the transaxial STC imaging of regional abdominal dysfunction. Other applications of the STC analysis of the present invention include:

- detecting regional autonomic dysfunction in aphasic or non-communicating nursing home residents;
- analyzing differences in unilateral STC to discriminate among, diagnose and treat transient ischemic attacks ("TIA"), reversible ischemic neurological deficits, and completed unilateral hemispheric stroke;
- analyzing STC regional differences to discriminate among, diagnose and treat various forms of migraine, cluster, tension, and other headache types;
- sympathetic tracking in wound healing with or without subsequent development of regional pain;
- post-traumatic evaluation of symptoms not otherwise detectable by standard diagnostic imaging procedures.

The apparatus, system and method of the present invention also find utility as an alarm system for children with intractable nocturnal enuresis (i.e., bed wetting).

Through the methods of the present invention, an underlying pathology, whether due to injury, illness or disease, may be objectively diagnosed, treated and monitored over time to determine progress. Periodic measurements may allow for one therapy to be measured against another. For example, the present invention provides objective criteria for comparing the efficacy of drug A against drug B to determine which best addresses a particular's subject's pain symptoms.

In addition, algorithmic analysis of baseline, bilateral and/or normative data enables to creation of a pain index, which, in turn, is highly valuable in determining a particular treatment protocol or regimen. The present invention further finds utility in the real-time quantification of pain, not only to determine the appropriate therapy but to discriminate legitimate pain patients from drug-seekers.

C. Illustrative Embodiments of the Present Invention:

Hereinafter, the present invention is described in more detail by reference to the Figures and Examples. However, the following materials, methods, figures, and examples only illustrate aspects of the invention and are in no way intended to limit the scope of the present invention. For example, while the present invention makes specific reference to arthroscopic procedures, it is readily apparent that the teachings of the present invention may be applied to other minimally invasive procedures and are not limited to arthroscopic uses alone. As such, methods and materials similar or equivalent to those described herein can be used in the practice or testing of the present invention.

EXAMPLES

The present invention provides a comprehensive system for the quantitative assessment of regional sympathetic sudomotor dysfunction which is useful in the objective assessment of sympathetically maintained pain syndromes; a painless electrodiagnostic method requiring no sensory stimulation or subjective reports by patients; a handheld, self-powered device with an LCD display; a rapid and simple test procedure with automatic report generation; a HHSIFDA Regulatory Class II non-invasive device; and a sympathetic skin assessment approved by Medicare and most insurance companies for procedure reimbursement.

In illustrative embodiment an improved meter and monitoring system of the present invention of the inventive is presented in FIGS. 1-4. FIGS. 1A, 1B, and 2A respectively depict top-down, perspective, plan views of a diagnostic device (100) designed in accordance with the principles of the present invention. Device (100) includes a housing (8) fabricated of upper (11) and lower (9) portions joined at seam (13) that together enclose the requisite circuitry and on-board power source. The proximal end of the device (100) is designed be held within the user's hand and thus may optionally be provided with finger flanges or recesses (not shown) to ensure a comfortable and secure grip. The distal end of the device (100) is characterized by a projecting sensor neck (15) and sensor head (4).

Figure 3A:
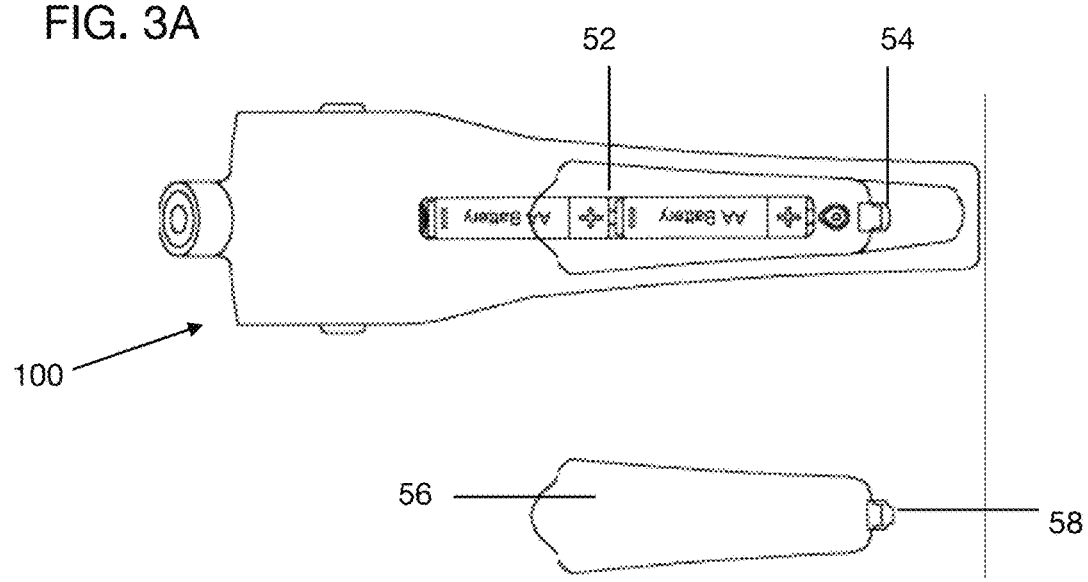
FIG. 3A is a side-elevational view of the underside diagnostic device (100) of FIG. 1A, with battery cover (56) removed.

As noted in FIG. 3A, the housing may be provided with a recess (52) for receiving one or more batteries. The battery recess may be accessed by removing cover (56). The cover can be securely reattached by coupling cover latch (58) with mating recess clip (54).

Figure 3B:
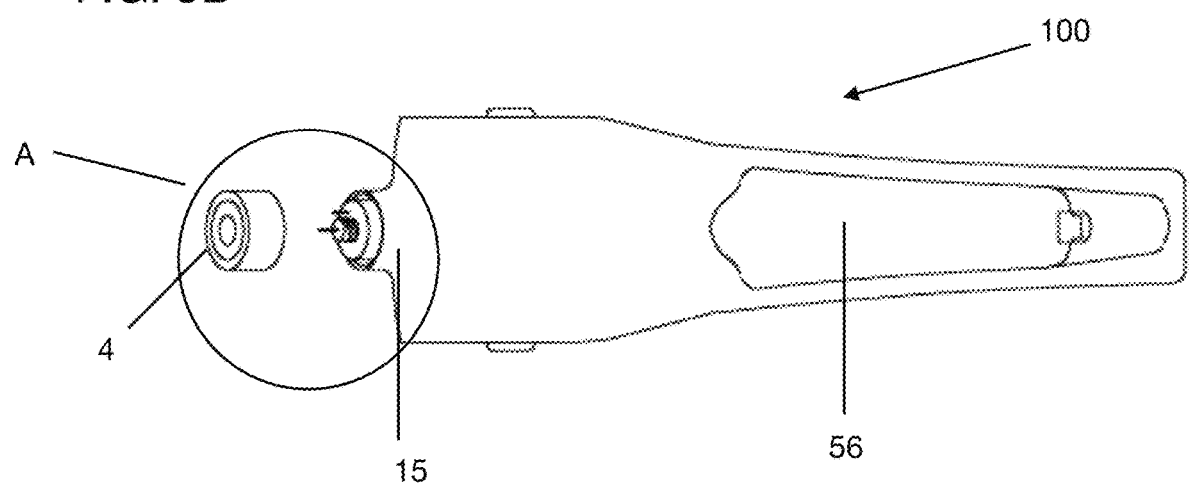
FIG. 3B is a side-elevational view of the underside of the diagnostic device (100) of FIG. 1A, with proximal battery cover (56) attached and distal electrode (4) removed.

As noted in FIG. 3B, the sensor head (4) may be detached and reattached from the housing as needed. As demonstrated in FIG. 3C, attachment in the depicted embodiment is achieved by mating the projecting pins (62) and annular groove (64) on the sensor neck (15) with corresponding aligned recesses and annular hub on the sensor head (not shown). However, it will be readily understood by the skilled artisan that the position of the respective coordinating elements (e.g., recessed slots and grooves that mate with assorted projecting protrusions, protuberances, tabs and splines) may be exchanged and/or reversed as needed.

Figure 3C:
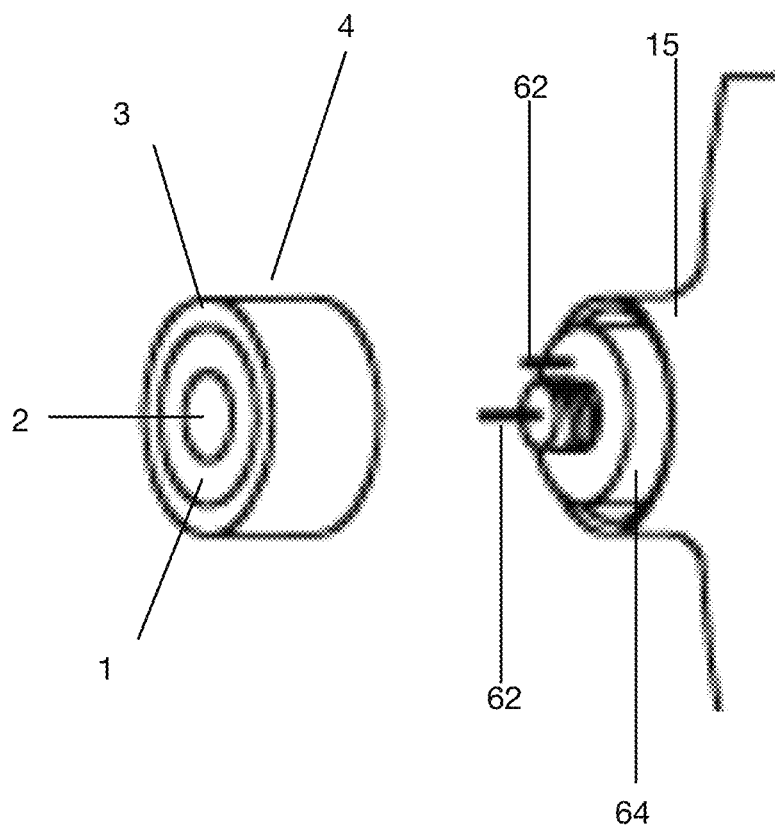
FIG. 3C is an expanded view of the objects of FIG. 3A at location A.

In a preferred embodiment depicted in FIG. 3C, the sensor head include a pair of concentric active electrodes (2, 3) separated by an insulating ring (1). This configuration is referred to a bipolar electrode in that its functions as both anode and cathode, "active" and "return".

Figure 1B:
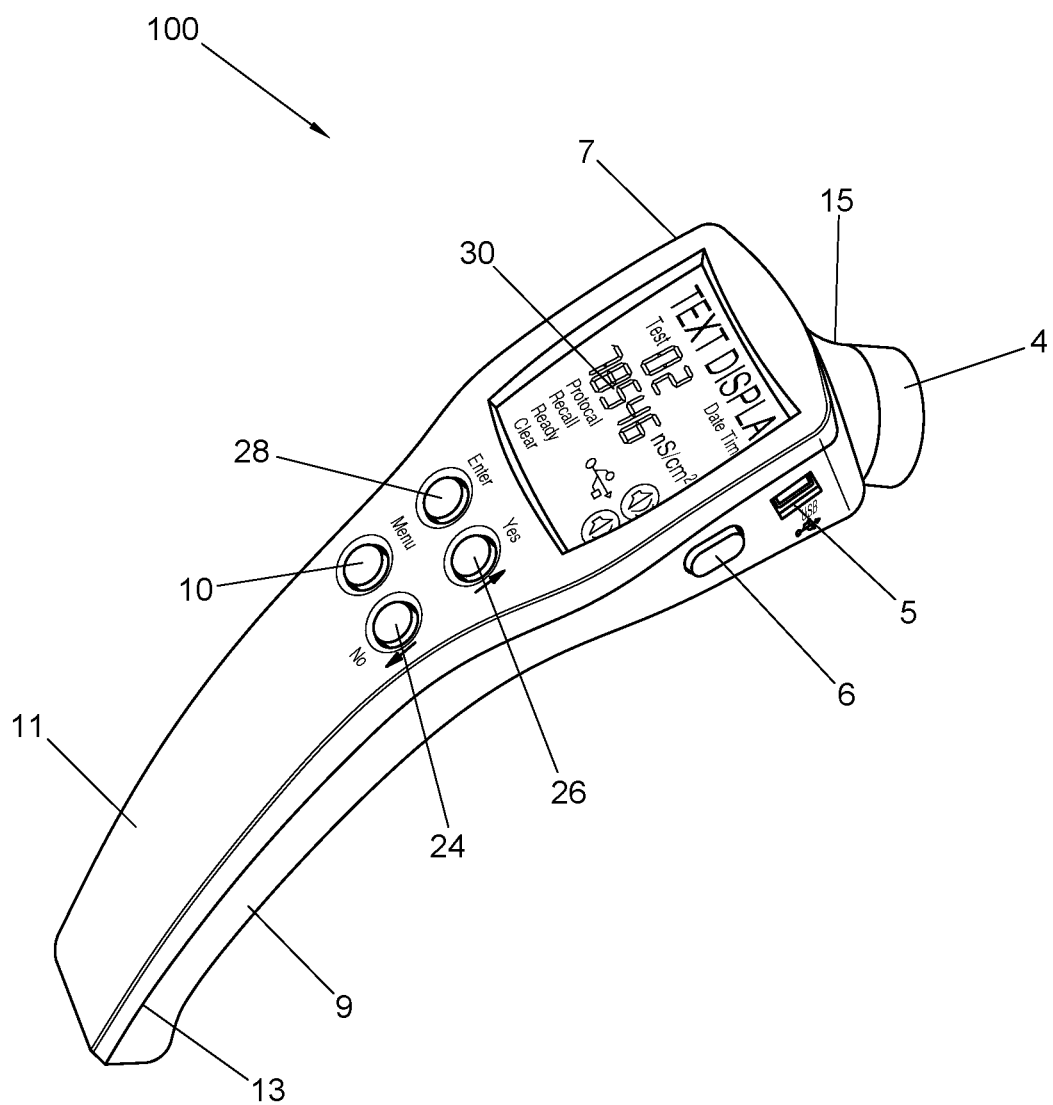
FIG. 1B is a photograph depicting a perspective view of the diagnostic device (100) of FIG. 1A.

Additional features of the diagnostic device depicted in FIGS. 1A and 1B are discussed in detail below.

The depicted device (100) uses a direct current (DC) measurement technique. The test current of the device (100) at the sensor head (4) is preferably a very low constant current of a maximum of 10 uA distributed over a 300 mm$^2$ area of the preferred sensor head (4) for an average of a maximum of 0.03 uA/mm$^2$. As discussed in greater detail above, this aspect of selective tissue conductance technology is known as spatial selectivity. However, as also noted above, the DC measurement technique can be replaced in the inventive system with a high frequency (preferably 1-100 kHz) alternating current signal to measure the current between the electrode components.

Preferred features of the inventive diagnostic device include, but are not limited to, the following:

Measurement Range: 1-80,000 nS/cm$^2$
Measurement Lower Limit: 1 nS/cm$^2$
Maximum Current Density: 0.03 uA/mm$^2$ (at electrode)
Output Display: Liquid Crystal
User Interface: 6 push button switches (keys)
Audible Indicators: integral speaker (optional headphone jack)
Interface: USB
Battery: 2 disposable (non-rechargeable) AA batteries
Battery Life: 70 hours of continuous operation. About 4 months with typical usage
Electric Shock Protection: Type B
Operation Mode: Continuous
Operating Environment: 50°-95° F. (10-35° C.), 10-90 relative humidity
Shipping and Storage Conditions: −40°-70° C., 0-90 relative humidity
Accessories: disposable electrodes; headphones; and USB cable However, it will be readily apparent that other power sources, audio outputs, interface schemes and the like are contemplated by the present invention.

Figure 2A:
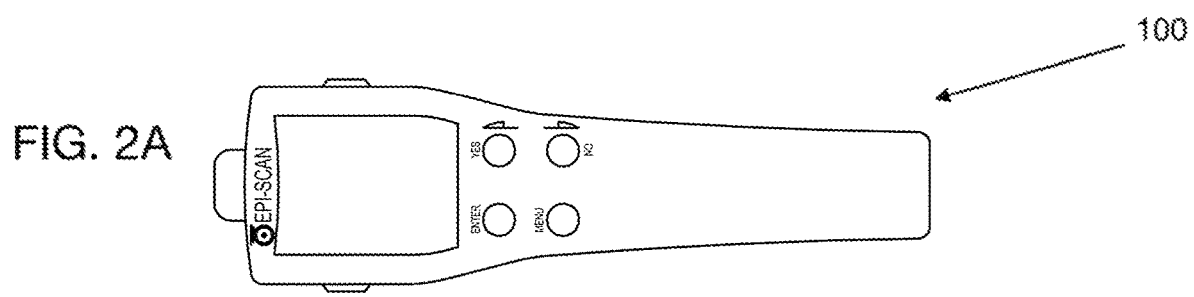
FIG. 2A is a plan view of the diagnostic device (100) of FIG. 1A.
Figure 2B:
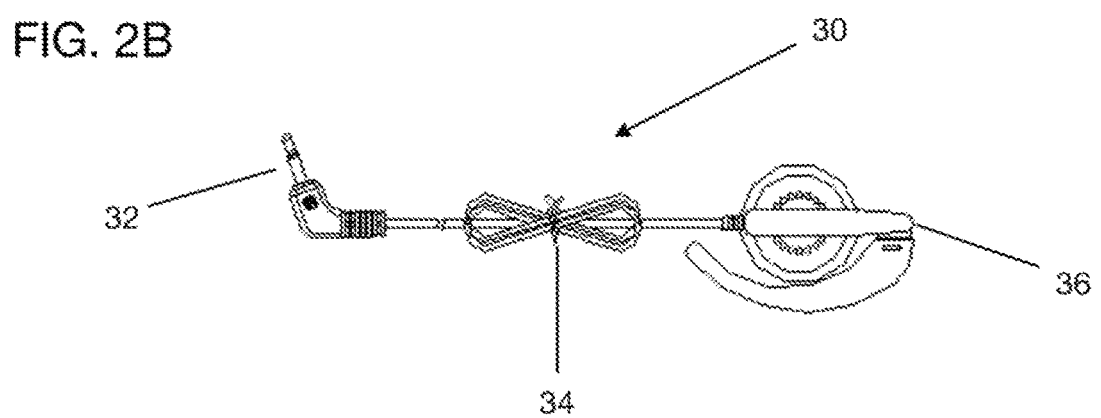
FIG. 2B is a plan view of a wired earphone that can connect to the diagnostic device (100) of FIG. 1A.
Figure 2C:
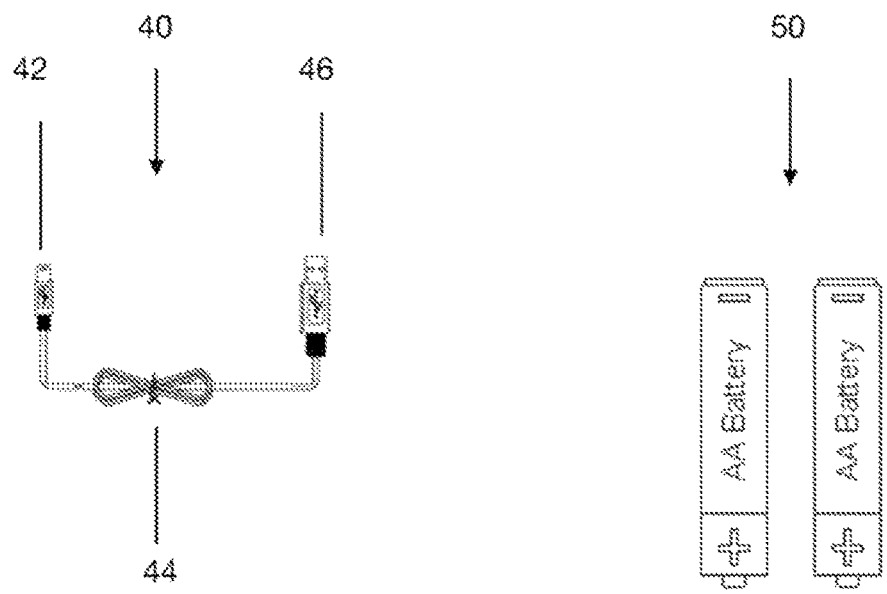
FIG. 2C is a plan view of a connecting cable that serves to connect the diagnostic device (100) of FIG. 1A.
Figure 2D:
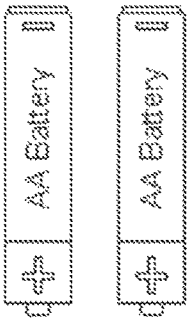
FIG. 2D is a plan view of a pair of disposable AA batteries that serve as the power source for the diagnostic device (100) of FIG. 1A.

The diagnostic device of the present invention may be packaged as a kit along with various coordinating accessories such as depicted in FIGS. 2B, 2C, and 2D. For example, the kit may include an external audio component, such as one or more wired or wireless earphones (30), headphones or speakers (not pictured). Earphones (30) for the device (100) may be needed in locations where the ambient noise level is high. Inserting the earphone connector (32) into the corresponding jack (7) on the device housing (8) disconnects the internal speaker. Note, the volume may need to be adjusted using up/down keys (24, 26).

The kit may further include a data transfer cord, such as depicted in FIG. 2C. In the illustrative embodiment, the respective ends include a type-C USB connector (46) and a micro-USB connector (42) coupled by cable (44). However, as noted above, alternate connector-port configurations are contemplated by the present invention, examples of which include, but are not limited to, firewire, HDMI, and e-SATA systems.

The kit may further include a power source, such as a pair of disposable AA batteries (50). However, as noted above, the power source may be rechargeable, for example in the form of a rechargeable battery pack that would be provided with the requisite associated charging cradle or charging cord(s). In an alternative embodiment, the diagnostic device may be fitted with a DC power jack capable of receiving power from a low voltage DC power source. Furthermore, alternating current (AC) power may be transformed to DC power by means of a wall-mounted transformer or 9V wall charger. In this embodiment, no AC power reaches the sensing head itself, thereby reducing the possibility and severity of electrical shock.

As noted above, each sensor head (4) is preferably used only once. In particular, it is recommended that a new sensor head (4) be used on each patient. In a preferred embodiment, the sensor head is designed as a replaceable and disposable diode. Using a new "testing head" for each patient improves sensitivity, extends the life of the system and avoids the issues of sterilization and contamination. Accordingly, the aforementioned kit may further include multiple sensor heads. Each sensor head may be identical or different, tailored for single parameter or multi-parameter measurement. In a preferred embodiment, each sensor head is separately wrapped in sterile packaging.

To remove a previously used sensor head (4), hold the outer edge by thumb and fingers and turn in a counterclockwise direction. To install the sensor head (4) onto housing (8), one should first remove it from its sterile wrapper. The center contact of the sensor head (4) is then placed over pin(s) (62) and in the annular groove (64) disposed in the sensor neck (15) of housing (8) of the inventive meter 2 and turned in a clockwise direction. When first installing a new sensor head, it is recommended that the user take a few test measurements in the "Ready" mode (described below) to ensure that the sensor head (4) is functioning properly and to become familiar with the appropriate positioning of the sensor head against the skin. While the results are not dependent on the amount of pressure, given that the conductance readings are expressed in terms of square centimeters (cm$^2$) of surface area, it is critical that the entire active surface (e.g., inner and outer electrodes, 2 and 3) be placed in contact with the skin with sufficient pressure. If the entirety of the active electrode surface is not touching the skin, the readings will be incorrect. By the same token, while too much pressure is unnecessary, too little pressure can give rise to erroneous results.

While the illustrated embodiments depict a rigid and fixed connection between sensor neck (15) and housing (8), the present invention contemplates a flexible and/or articulated joint couplings, ranging from a simple single plane hinge to a ball-and-socket joint that affords a full 360° range of motion. Such flexible couplings ensure complete contact with the skin, particularly over contoured portions of the body such as the shoulders, knees, elbows, etc.

To take measurements with the diagnostic device (100) of the present invention, one should place the sensor head (4) against the skin area to be measured, making sure the entire active surface (i.e., electrodes 2 and 3 and insulator 1) is placed in contact with the skin. The electrode should not be rocked during testing. Apply just sufficient pressure to ensure a good contact; too much pressure is unnecessary. Listen for the confirmation tone indicating that the test measurement is complete. This step generally takes about one half second and no more than two seconds.

Figure 4:
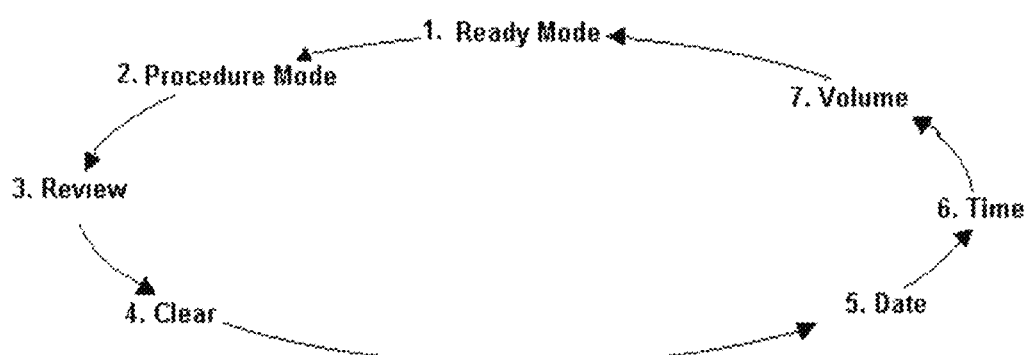
FIG. 4 is a loop illustration of the different operating modes and utilities that may programmed into a diagnostic device of the present invention.
Figure 5:
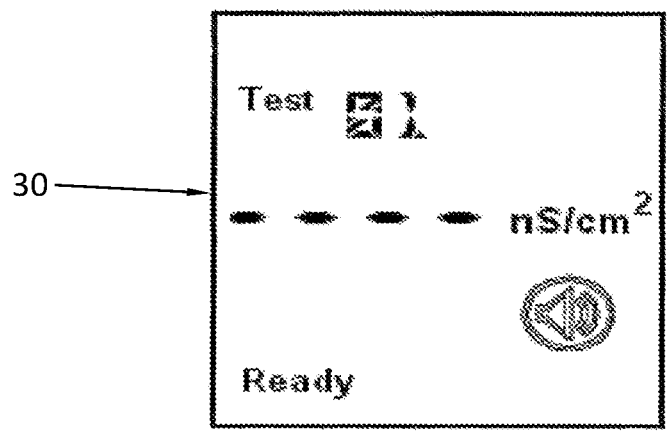
FIG. 5 depicts an illustrative display screen for a diagnostic device of the present invention, in "Ready" or "Manual" Mode.

Pressing the "menu" key (10) allows the operator to scroll through different programmed operating modes and utilities in a loop, as illustrated in FIG. 4. Exemplary operating modes and utilities include, but are not limited to:

The Ready Mode (or Manual Mode) is used to make one or more individual measurements and temporarily store the data. An exemplary display screen (30) of the device (100) in Ready Mode is illustrated in FIG. 5.

Figure 6:
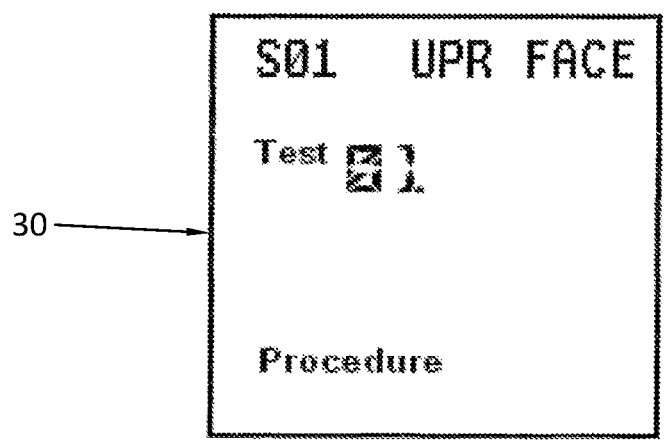
FIG. 6 depicts an illustrative display screen for a diagnostic device of the present invention, in "Procedure" Mode.

The Procedure Mode is used to make measurements according to preset programmed montages and these can also be reviewed and uploaded to a computer. An exemplary display screen (30) of the device (100) in Procedure Mode is illustrated in FIG. 6.

Figure 7:
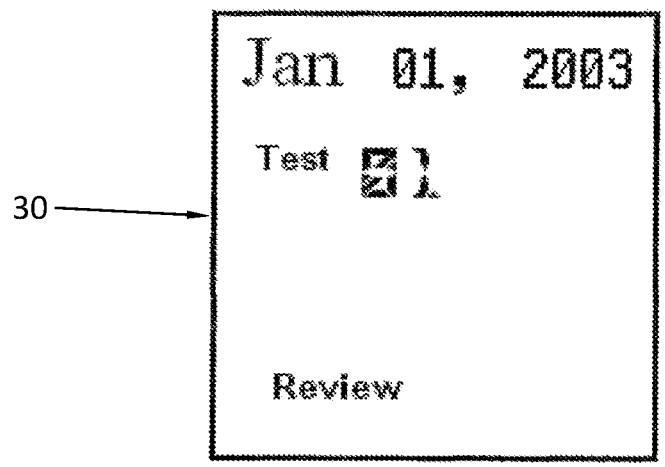
FIG. 7 depicts an illustrative display screen for the "Review" utility in a diagnostic device of the present invention.

The Review utility is used to recall measurements taken in the procedure mode. An exemplary display screen (30) of the device (100) in Review Mode is illustrated in FIG. 7.

Figure 8:
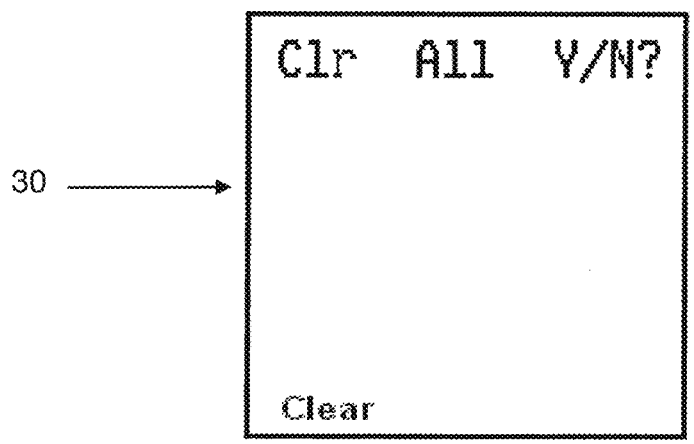
FIG. 8 depicts an illustrative display screen for the "Clear" utility in a diagnostic device of the present invention.

The Clear utility is used to delete stored tests. An exemplary display screen (30) of the device (100) in Clear Mode is illustrated in FIG. 8.

Figure 9:
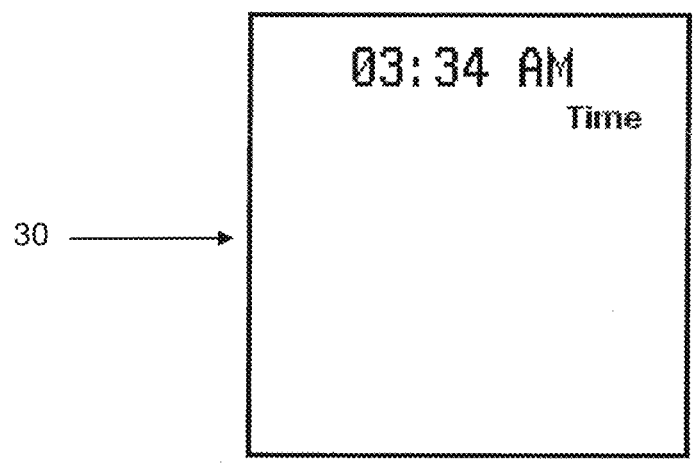
FIG. 9 depicts an illustrative display screen for the "Time/Date Setting" utility in a diagnostic device of the present invention.

The Time/Date setting utility is used to set the date. An exemplary display screen (30) of the device (100) in Time/Date Setting Mode is illustrated in FIG. 9.

Figure 10:
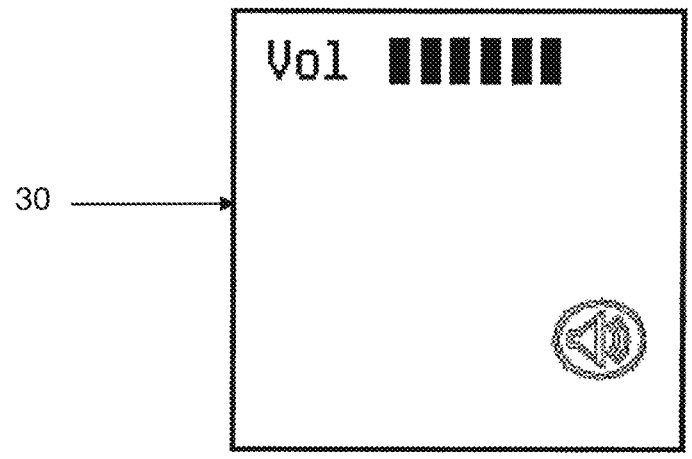
FIG. 10 depicts an illustrative display screen for the "Volume" utility in a diagnostic device of the present invention.
Figure 12:
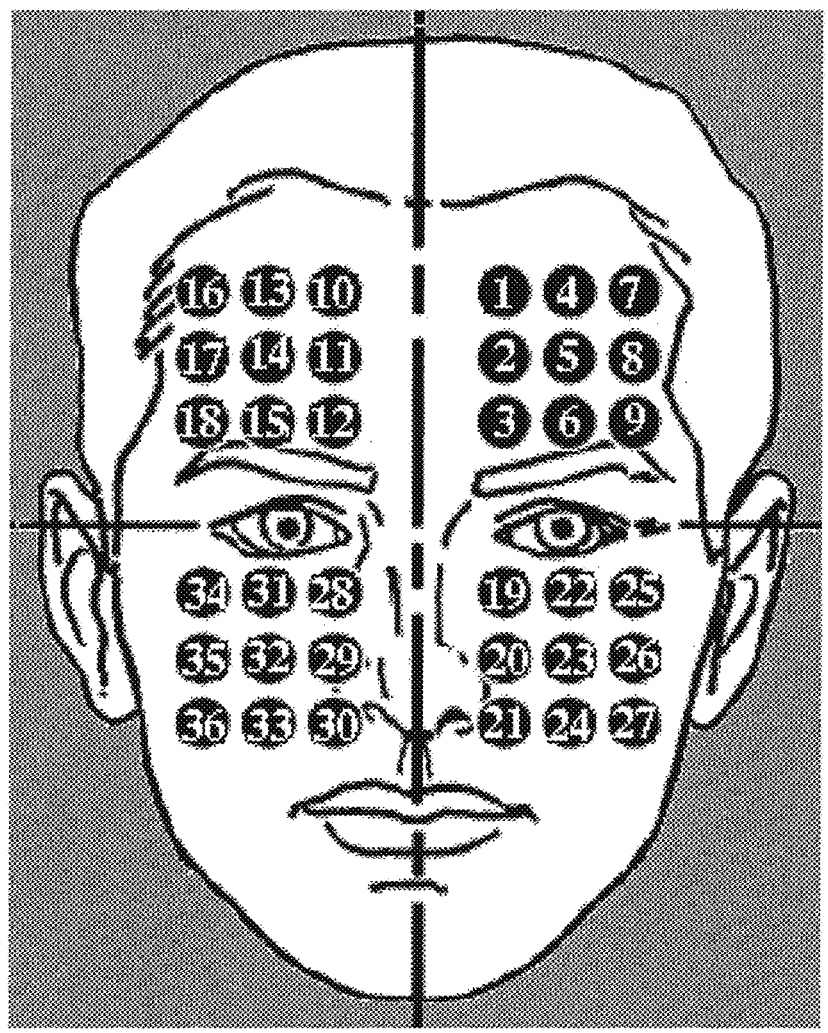
FIG. 12 depicts the 6×6 matrix of measurement sites as well as measurement sequence for assessment of upper facial tissue, designated as preset montage S01 (UPR-FACE).
Figure 13:
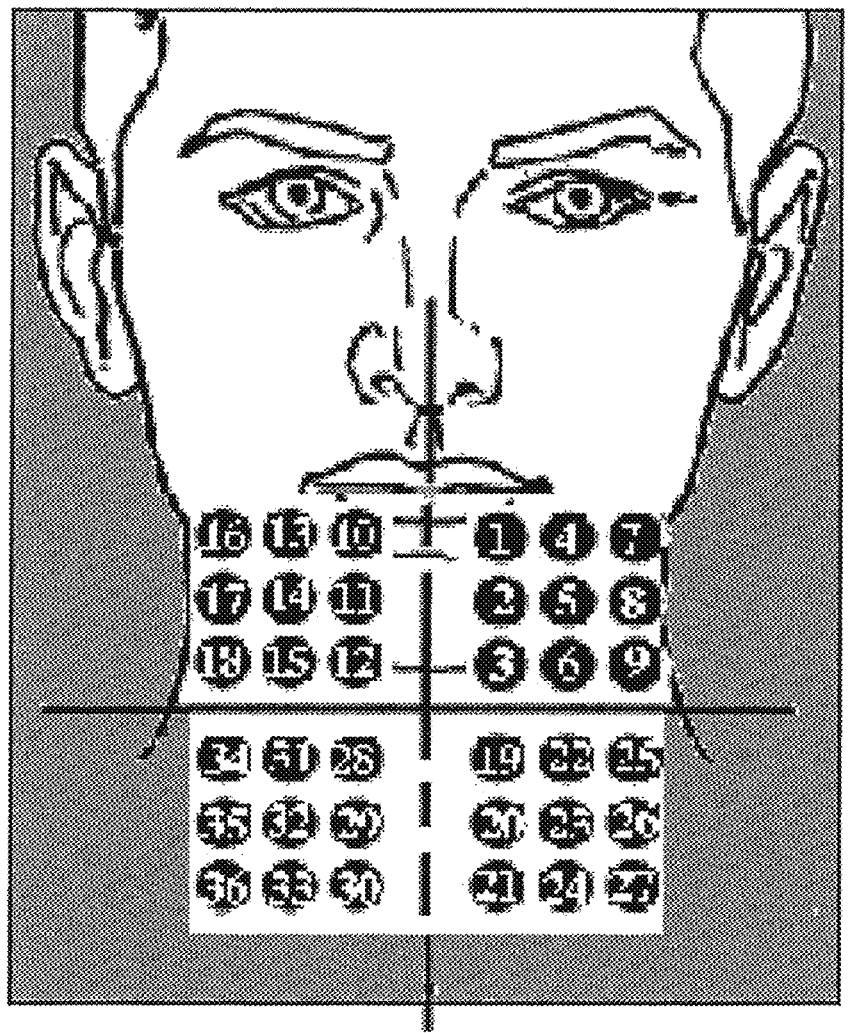
FIG. 13 depicts the 6×6 matrix of measurement sites as well as measurement sequence for assessment of anterior neck tissue, designated as preset montage S02 (ANT-NECK).
Figure 14:
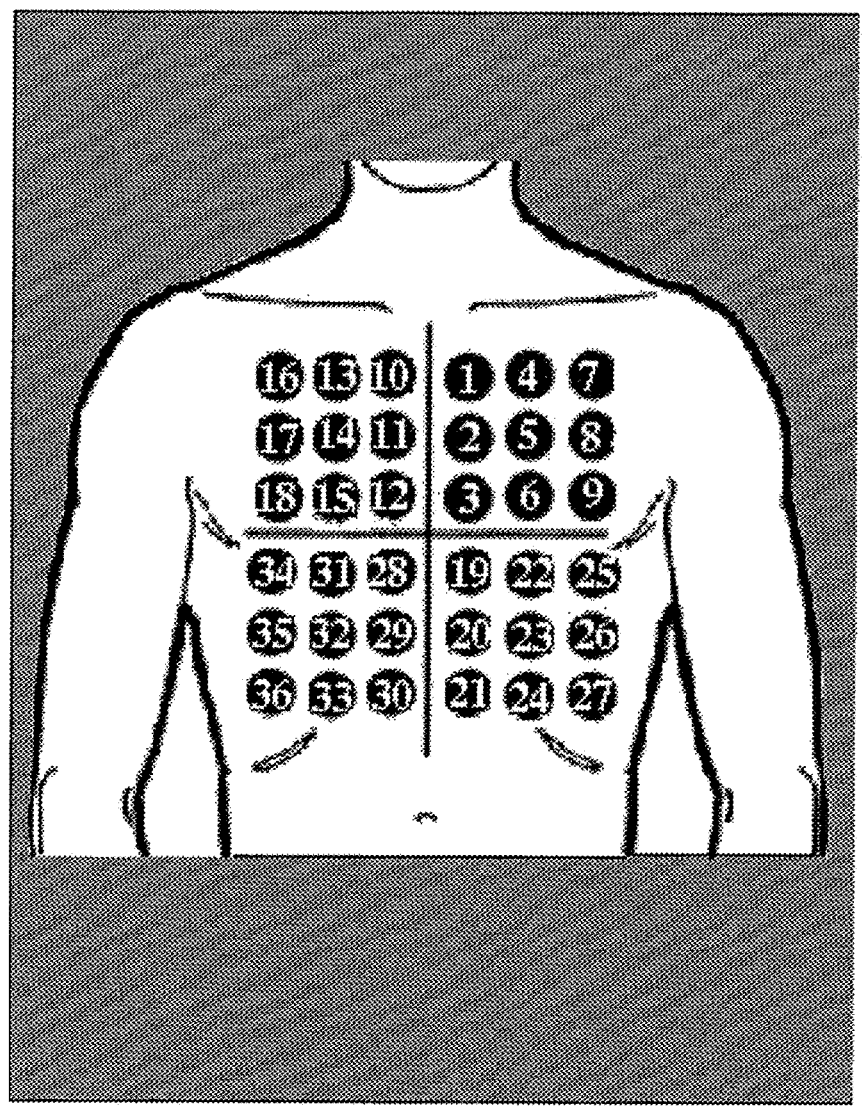
FIG. 14 depicts the 6×6 matrix of measurement sites as well as measurement sequence for assessment of chest tissue, designated as preset montage S03 (CHEST).
Figure 15:
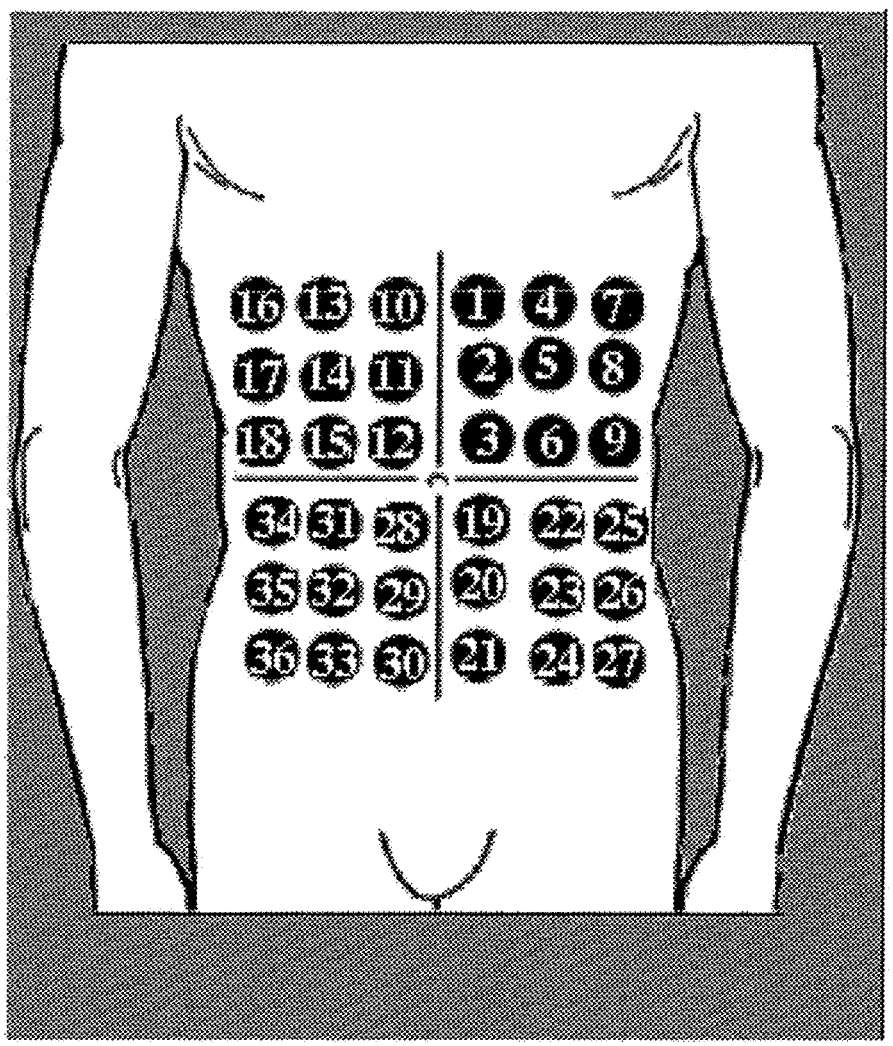
FIG. 15 depicts the 6×6 matrix of measurement sites as well as measurement sequence for assessment of abdominal tissue, designated as preset montage S04 (ABDOMEN).
Figure 16:
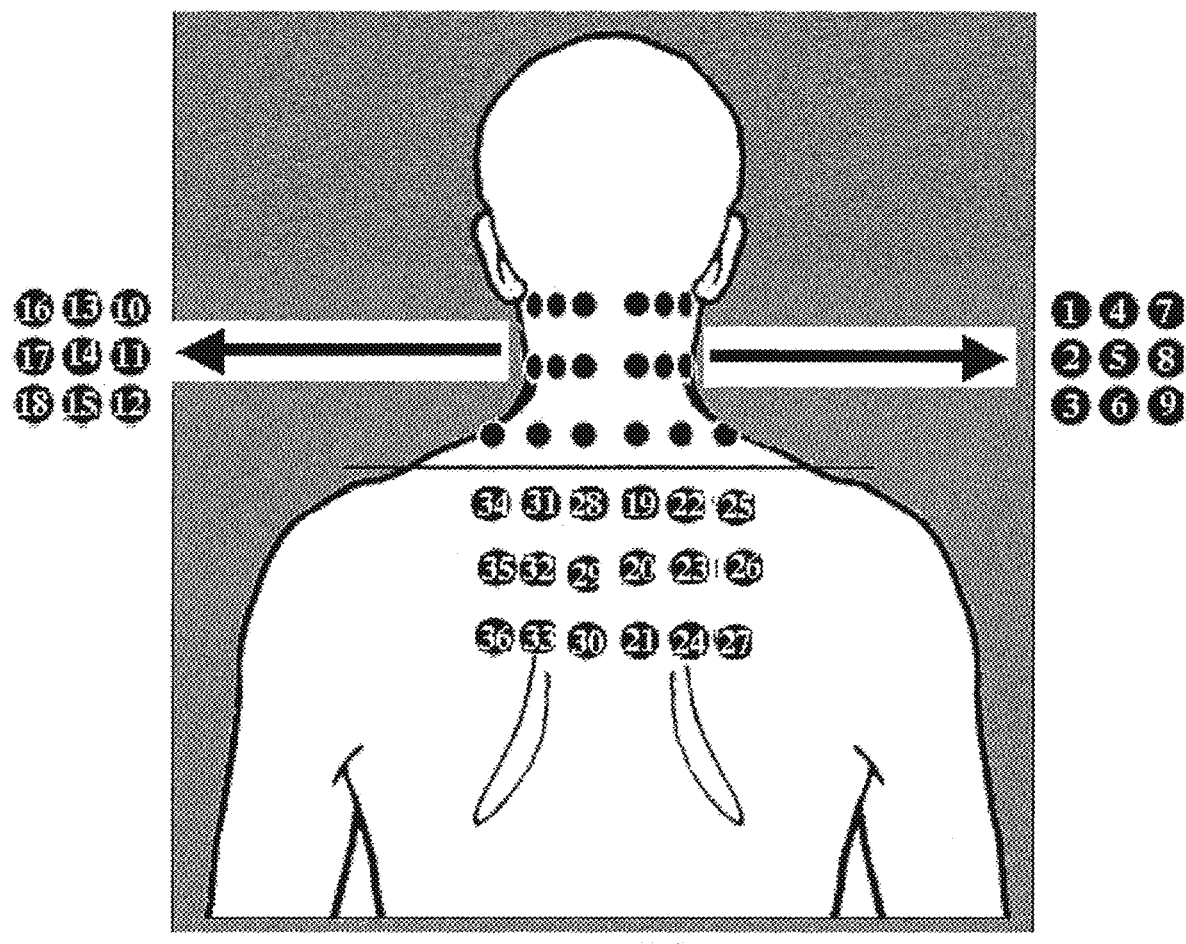
FIG. 16 depicts the 6×6 matrix of measurement sites as well as measurement sequence for assessment of cervical spinal tissue, designated as preset montage S05 (C-SPINE).
Figure 17:
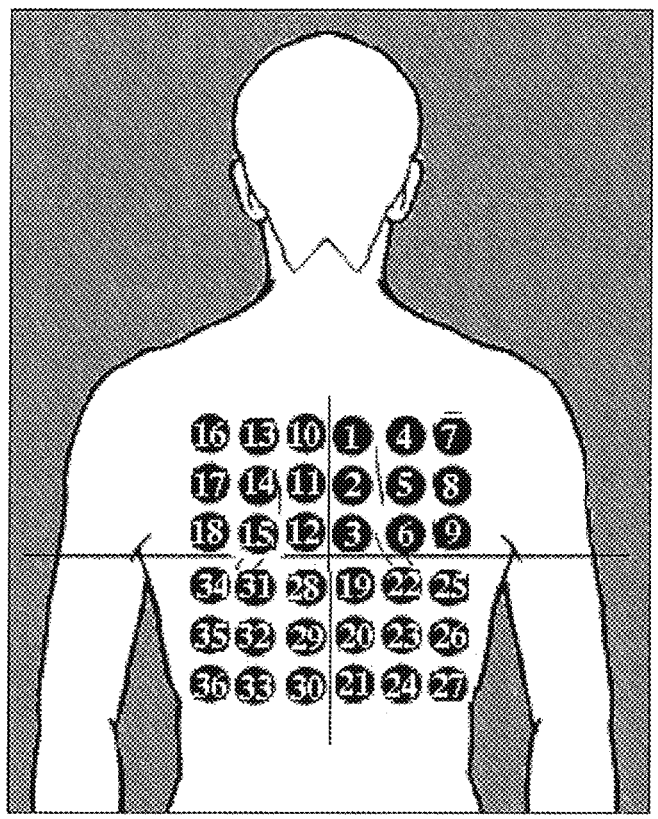
FIG. 17 depicts the 6×6 matrix of measurement sites as well as measurement sequence for assessment of thoracic spinal tissue, designated as preset montage S06 (TH-SPINE).
Figure 18:
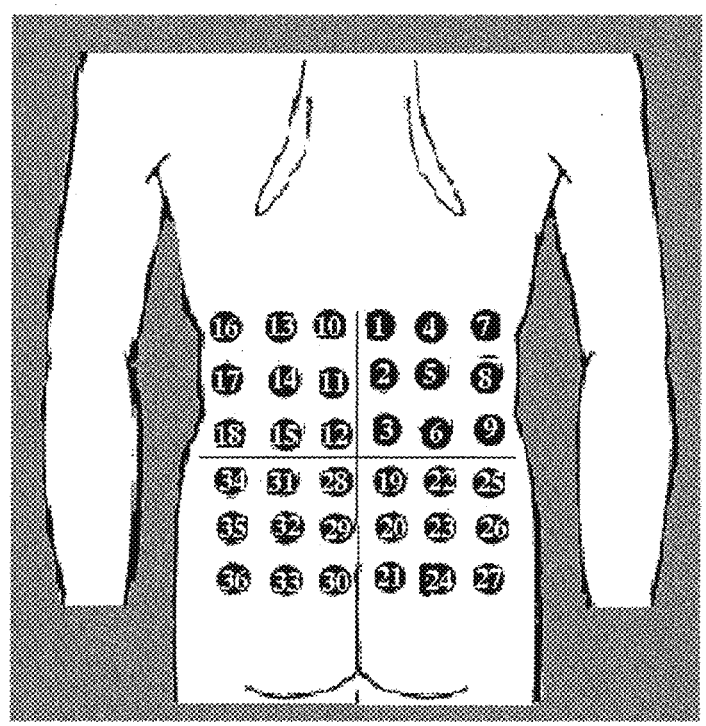
FIG. 18 depicts the 6×6 matrix of measurement sites as well as measurement sequence for assessment of lumbosacral spinal tissue, designated as preset montage S07 (LS-SPINE).
Figure 19:
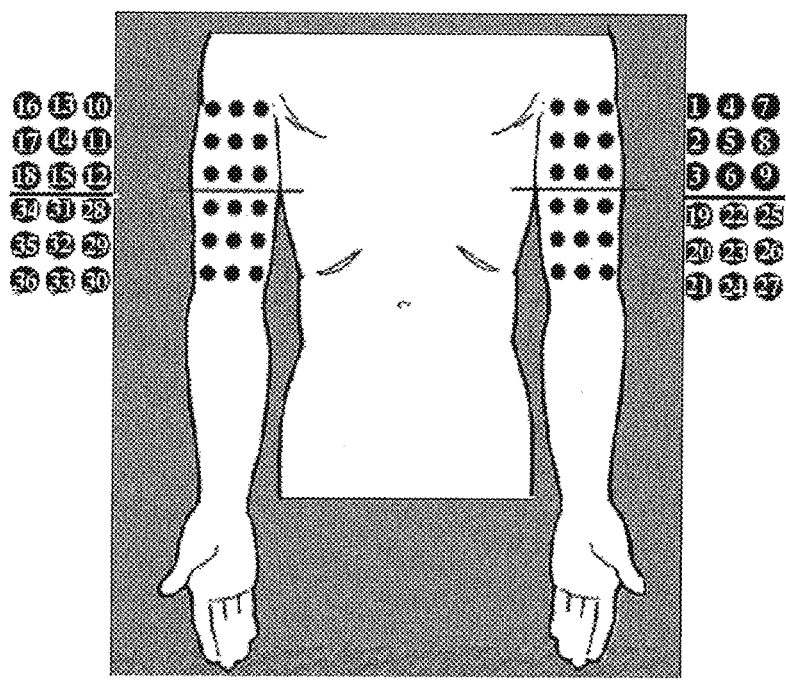
FIG. 19 depicts the 6×6 matrix of measurement sites as well as measurement sequence for assessment of the anterior of the upper arms, designated as preset montage S08 (UP-ARM-AN).
Figure 20:
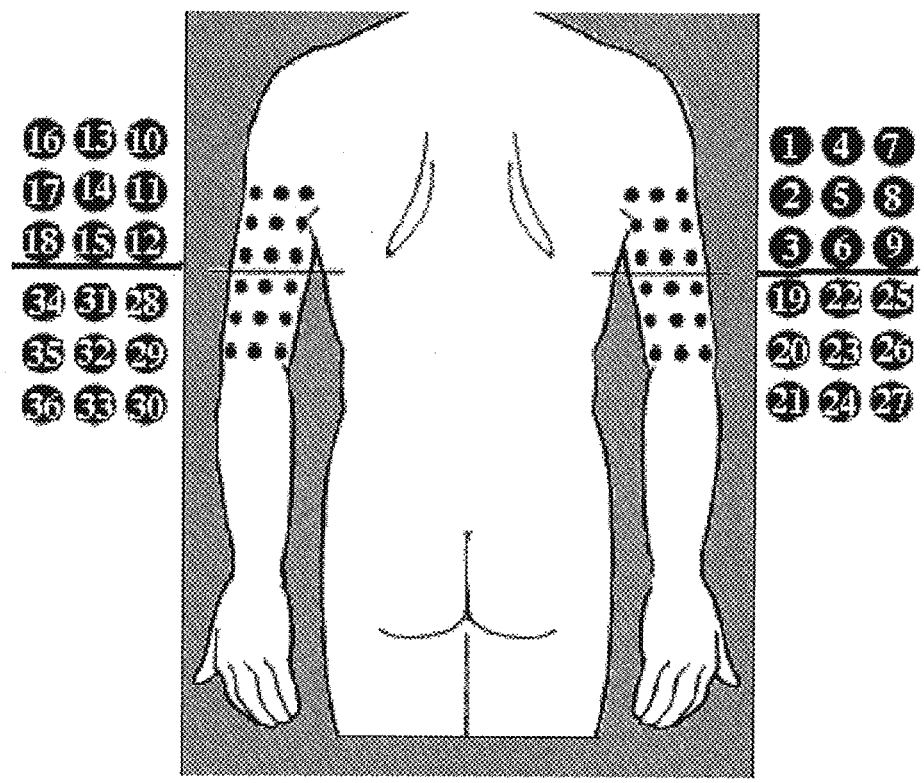
FIG. 20 depicts the 6×6 matrix of measurement sites as well as measurement sequence for assessment of the posterior of the upper arms, designated as preset montage S09 (UPARM-PO).
Figure 21:
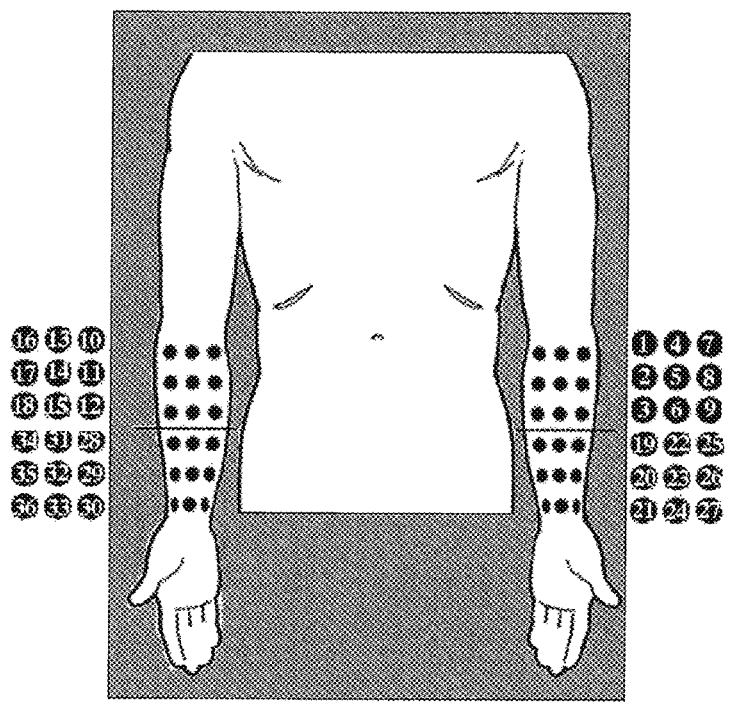
FIG. 21 depicts the 6×6 matrix of measurement sites as well as measurement sequence for assessment of the anterior of the forearms, designated as preset montage S10 (FRARM-AN).
Figure 22:
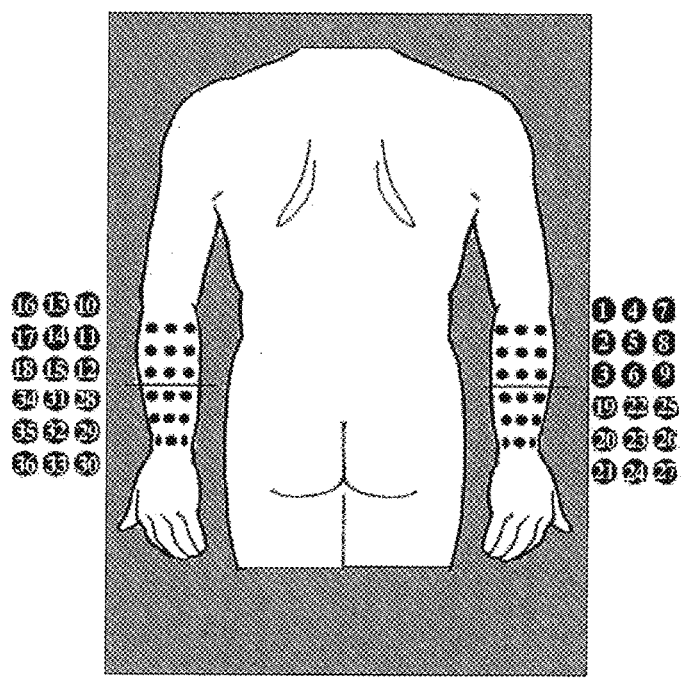
FIG. 22 depicts the 6×6 matrix of measurement sites as well as measurement sequence for assessment of the posterior of the forearms, designated as preset montage S11 (FRARM-PO).
Figure 23:
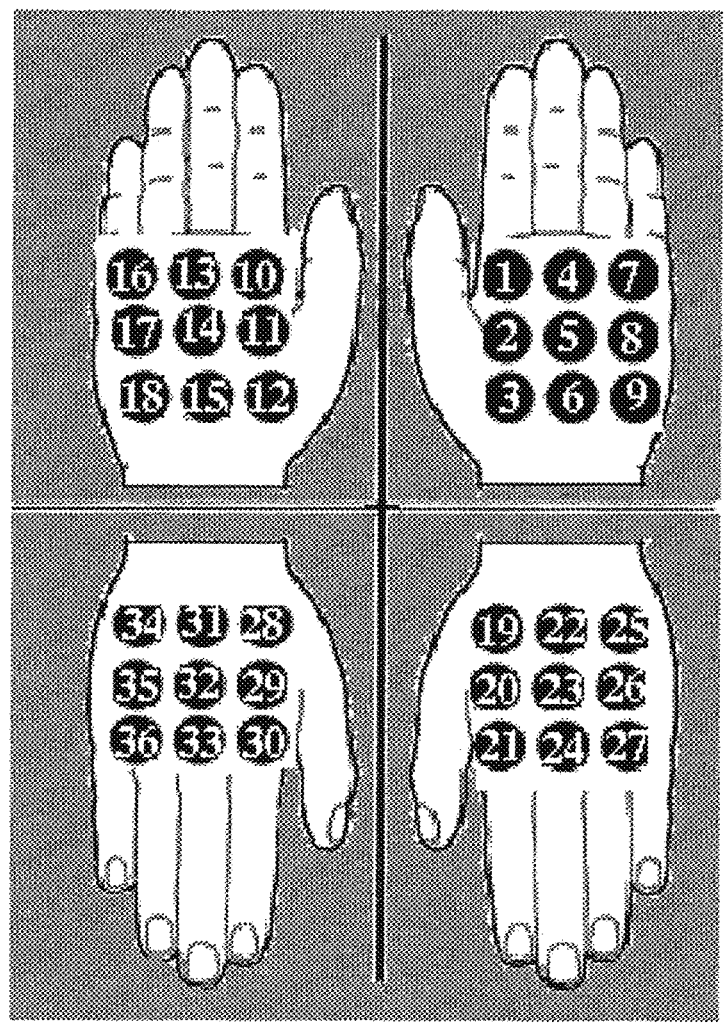
FIG. 23 depicts the 6×6 matrix of measurement sites as well as measurement sequence for assessment of the palmar and dorsal surfaces of the hands, designated as preset montage S12 (HANDS).
Figure 24:
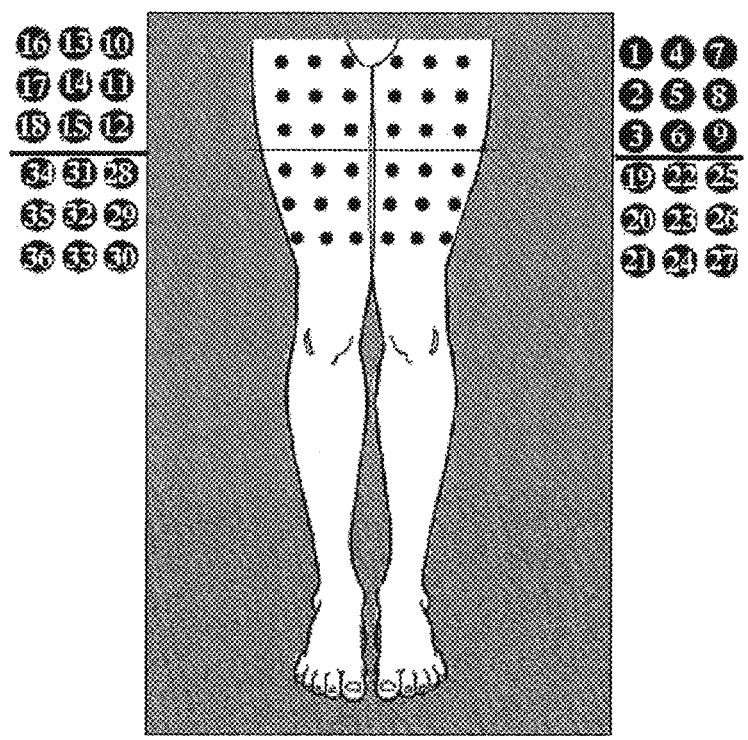
FIG. 24 depicts the 6×6 matrix of measurement sites as well as measurement sequence for assessment of the anterior of the thighs, designated as preset montage S13 (THIGH-AN).
Figure 25:
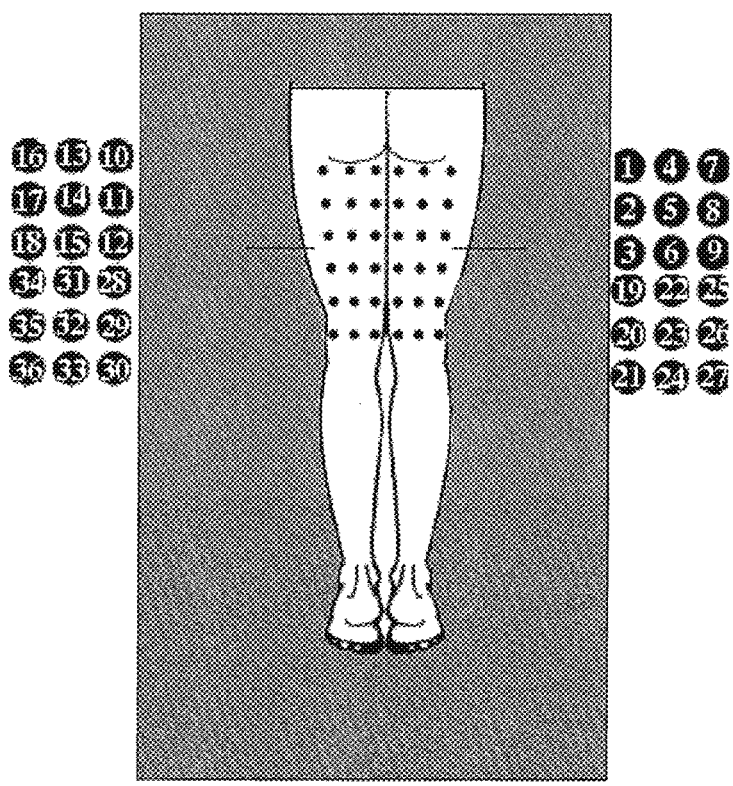
FIG. 25 depicts the 6×6 matrix of measurement sites as well as measurement sequence for assessment of the posterior of the thighs, designated as preset montage S14 (THIGH-PO).
Figure 26:
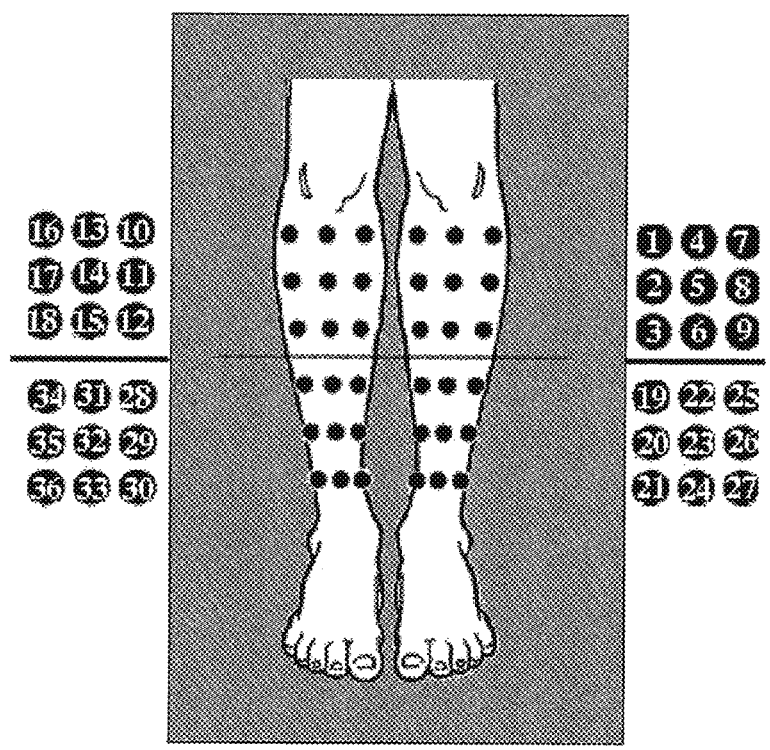
FIG. 26 depicts the 6×6 matrix of measurement sites as well as measurement sequence for assessment of anterior of the lower legs, designated as preset montage S15 (LOLEG-AN).
Figure 27:
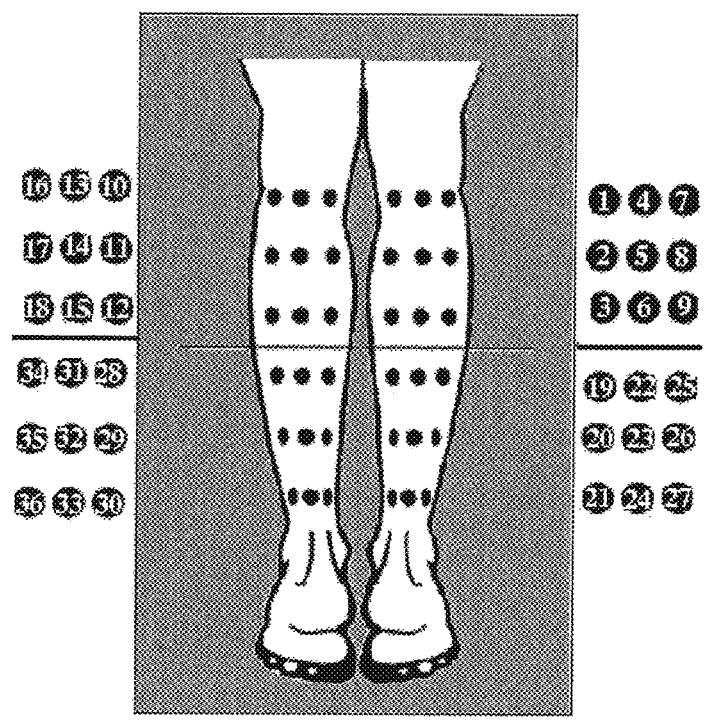
FIG. 27 depicts the 6×6 matrix of measurement sites as well as measurement sequence for assessment of posterior of the lower legs, designated as preset montage S16 (LOLEG-PO).
Figure 28:
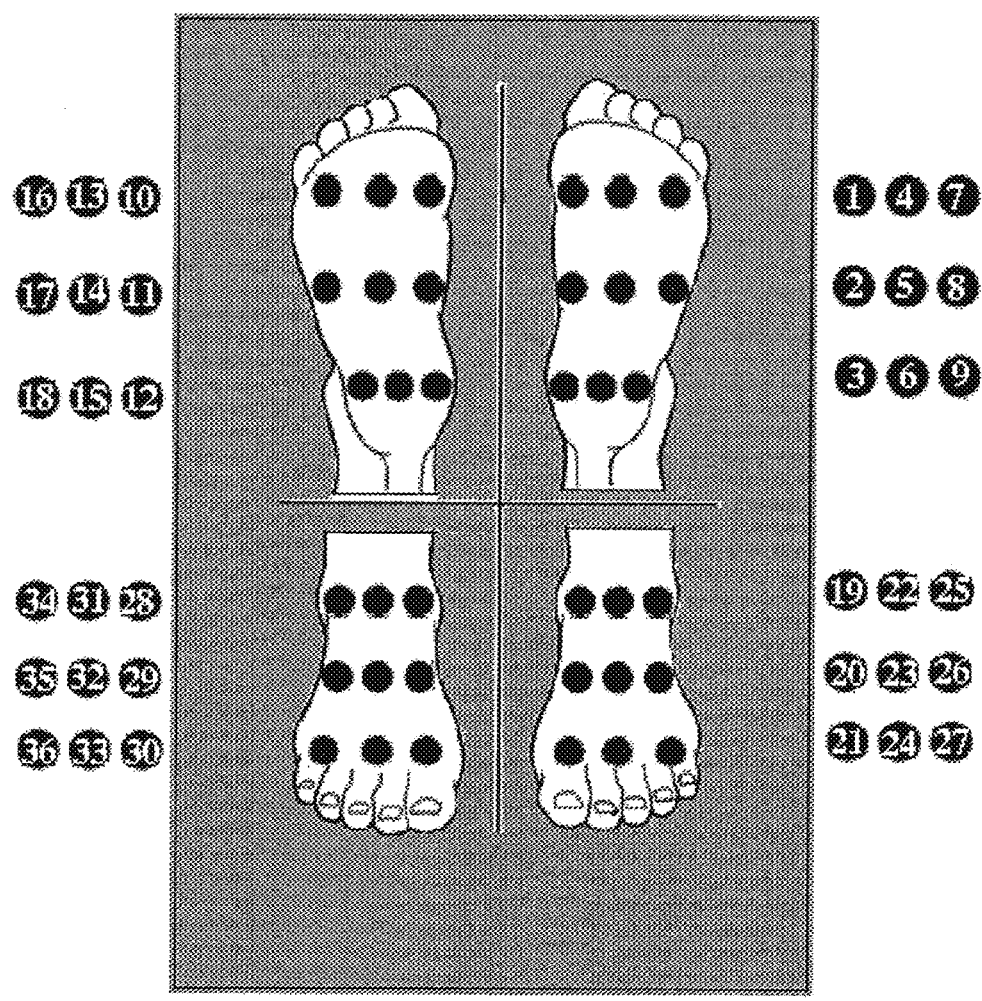
FIG. 28 depicts the 6×6 matrix of measurement sites as well as measurement sequence for assessment of the plantar and dorsal surfaces of the feet, designated as preset montage S17 (FEET).

The Volume utility is used to set the volume of the internal speaker of the device (100), or alternatively the volume output to an external audio source, such as the earphones (30). An exemplary display screen (30) of the device (100) in Volume Setting Mode is illustrated in FIG. 10.

Illustrative instructions for each of the above exemplary operating modes and utilities are set forth below:

Ready Mode:

The following are exemplary "Quick Instructions" in Ready Mode: First, make sure the device (100) is in Ready Mode. Second, place the distal end of the sensor head (4) against the skin and hold for half a second. Third, listen for the beep and review the measurement. Fourth, by using the Up and Down keys, 24 and 26, previous measurements can be reviewed.

Exemplary "Step-By-Step Instructions" for the programmed Ready Mode are as follows: First, toggle through the options by repeatedly pressing the "Menu" key (10) until the device (100) displays the "Ready Mode" as illustrated in FIG. 5. Second, after the distal end of the sensor head (4) (i.e., electrode assembly: elements 1-3) has been held against the skin for approximately one-half second, a tone indicates the completion of the measurement. Remove the sensor head (4) from the skin and the STC value will be displayed. Further measurements can now be performed.

Note that a Gieger type tone is also provided which is proportional to the STC values between 0 and 100 nS/cm$^2$. Any STC values higher than 100 nS/cm2 will have the same tone. The device (100) will continue to update its clicking tone but will not the display as long as the electrode is placed on the skin. This allows the user to use the instrument to scan a body region using the Gieger clicking tone to locate areas of high conductance.

The Ready Mode can be used to take any additional individual measurements by repeating Step 2. The test number assigned by the device (100) increases incrementally as additional tests are performed. In the Ready Mode, the diagnostic device (100) of the present invention will retain the measured STC values until it automatically turns off. The measurements taken in Ready Mode can be recalled for review by using the Up or Down buttons, 24 and 26.

When the power turns off or when a new mode is selected, any data previously stored while in the Ready Mode will be lost. If the Menu key (10) is accidentally pressed in Ready Mode, an Exit Yes/No prompt will display. If the "yes" key (26) is pressed, the test data will be lost and the device (100) will revert back to Ready Mode. If the "no" key (24) is pressed, the test can be continued.

Procedure Mode:

The Procedure Mode is used when choosing from as many as eighteen or more pre-programmed montages that may optionally be stored in the device (100). A sample list of pre-programmed montages is provided below in Table 1. However, the present invention is not limited to this specific set of montages and thus the device (100) may periodically be updated to incorporate additional and/or modified montages as needed. In any event, the Procedure mode is useful when focusing on a certain body region so that it is easy to do an assessment and generate a report, which will help in finding any abnormality. The Procedure Mode assists doctors in reviewing the results and in quickly generating an accurate report.

The following are "Quick Instructions" for the Procedure Mode. First, select a pre-programmed montage. Second, enter the Montage ID from Table 1. Third, take a preliminary first set of three "BioCheck" values. Fourth, take an array of thirty-six STC Values of the body region to be tested. Fifth, take a final three post-procedure "BioCheck" values.

Illustrative "Step-by-Step Instructions" for the programmed Procedure Mode are as follows:

1. Toggle through the options by repeatedly pressing the Menu key (10) until the device (100) displays the Procedure Mode such as depicted in FIG. 6.
2. At the top of the screen, a flashing message will appear which contains a procedure code (e.g., S01 to S18), followed by the abbreviated name of the body region to be tested. Table 1 below presents a list of the procedure codes for each of eighteen pre-programmed montages. The abbreviated name of the procedure and the full name of the region to be tested are also provided.

TABLE I

PROCEDURE CODES
Preprogrammed Montages

| | | |
|---|---|---|
| S01 | UPR FACE | Upper Face |
| S02 | ANT NECK | Mandible & Anterior Neck |
| S03 | CHEST | Chest |

TABLE I-continued

PROCEDURE CODES
Preprogrammed Montages

| S04 | ABDOMEN | Abdomen |
| S05 | C SPINE | Cervical Spine |
| S06 | TH SPINE | Thoracic Spine |
| S07 | LS SPINE | Lumbosacral Spine |
| S08 | UPARM AN | Upper Arms, Anterior View |
| S09 | UPARM PO | Upper Arms, Posterior View |
| S10 | FRARM AN | Forearms, Anterior View |
| S11 | FRARM PO | Forearms, Posterior View |
| S12 | HANDS | Hands (Palmar & Dorsal) |
| S13 | THIGH AN | Thighs, Anterior View |
| S14 | THIGH PO | Thighs, Posterior View |
| S15 | LOLEG AN | Lower Legs, Anterior View |
| S16 | LOLEG PO | Lower Legs, Posterior View |
| S17 | FEET | Feet, (Plantar & Dorsal) |
| S18 | GRADIENT | Linear Gradient (2 sets of 20) |

3. Use the Up or Down keys (24, 26) to select the desired procedure, then press the Enter key (28).
4. After selecting the appropriate preprogrammed test, the device (100) may prompt the entry of a procedure identification code and then switch to the Entry Mode. This feature allows the user to enter a file or patient identification number by pressing the Up or Down keys (24, 26) until the value for each of the digits has been selected. After each digit is changed from zero to its new value, press the Enter key (28).
5. After entering the Identification Number, the device (100) may prompt the user to confirm the entry.
6. If the Identification Number is correct, press the Yes (Up) key (26); if incorrect, press No (Down) key (24) and re-enter the number. Once the Identification Number has been accepted, the ID will be stored in the test data file and maintained in the on-board memory until downloaded or transmitted to an external storage device. The present invention contemplates both wired and wireless connections to local, networked or cloud storage devices.
7. Now the device (100) is ready to a series of preliminary instrument test values known as "BioCheck". While the illustrative examples refer to Biocheck values 1, 2 and 3, it will be readily apparent to the skilled artisan that greater or fewer measurements may be utilized. The BioCheck confirms that the sensor head (4) is operating properly. In the context of the present invention, preferred BioCheck measurements made on the right palm, left palm, and the Mid Frontal Polar Region (i.e., the middle of the patient's forehead). One or more measurements must have a positive value. If all are zero, an error message will display and will prompt the user to check the device (100) and repeat the procedure.
8. After the sensor head (4) has been held against the skin for approximately one-half second, a tone indicates the completion of the measurement and the measured value at the time of the tone will be entered, thus preventing the readings from being skewed by the ionophoresis effects which, as discussed above, may be produced by any continued application of the DC current to the skin after the tone. The sensor head (4) must now be removed from the skin. The display screen (30) will display a message asking the user to indicate whether the user accepts the value displayed. This is a double check to confirm that the measurement was made correctly. Press the Yes (Up) key (26) or side auxiliary keys to accept the measurement.
9. If the No (Down) key (24) is pressed, the data is discarded and a new measurement can be made. It is also possible to obtain a valid measurement that is below the threshold of 1 $nS/cm^2$. This is observed by pressing the sensor head (4) against the skin and not receiving a tone for an STC measurement value, and will be entered as a zero value. Pressing the Enter key (28) will store this value as zero and continue to the next measurement.
10. Before collecting the main body of the data in the Procedure Mode, the user is advised to make BioCheck measurements of the right palm, left palm, and Mid Frontal Polar region. The BioCheck measurements are taken to ensure the sensor head (4) is working before and after a test.
11. The main portion of each examination consists of a series of measurements made along a pattern of an equal number of vertical and horizontal lines, forming a grid optionally composed of thirty-six points. As noted above, this is referred to herein as a "Montage". Each of measurement site is identified by its position on one of the horizontal rows (e.g., R1 to R6) and one of the six vertical columns (e.g., C1 to C6). The resulting name of each site is therefore expressed in terms of row number and column number, e.g., R1C6. Illustrative thirty-six measurement point grids for the exemplary preprogrammed body locations recited in Table 1 are depicted in FIGS. 11-28 and discussed in greater below. Note, however, that while the examples make reference to a 6×6 matrix of 36 measurement sites, other matrices are contemplated, including both square and rectangular grids comprised of 3-8, preferably 4-6 rows and columns. In any measurement set, normative data from 20 points is used to establish a sample. Accurate diagnosis of differences in data can be statistically inferred from this N.
12. After a test montage is completed, the BioCheck screen will reappear and the biocheck measurements, e.g., of the right palm, left palm, and forehead, should be repeated.
13. After all of the measurements are made, appropriate for the procedure selected, the message "Test Done" may appear at the top of the screen (30). This message will flash alternately with an instruction to "Press A Key". As soon as any key is pressed, the procedure is closed with the measurements stored and the function of the device (100) is returned to the Procedure Mode, in preparation for the next test session. In this regard, it is further noted that:
   a. The test number increases incrementally as further tests are performed.
   b. Tests stored in the device (100) can be reviewed on the device, for example on display screen (30). The test will be identified according to the date and then the patient ID number of the test performed that day. Each day the tests are stored sequentially. Once the tests have been uploaded to an external computer or database, the ID Number can be used for identification, for example a search term to identify previous results.
   c. If the Menu key (10) is accidentally pressed in Procedure Mode the Exit Yes/No prompt will display. If the Yes key (26) is pressed the present test data will be lost and the device (100) will revert back to Procedure Mode. If the No key (24) is pressed, the test can be continued.

14. After the final measurements are made, the automatic shutdown feature of the device (100) will turn off the power after a predetermined idle duration, typically two to three to five minutes.

Review Utility Mode:

To recall and review the aforementioned Procedure Mode tests stored on the device (100), the Review Utility Mode is used. Tests stored in the device (100) can be reviewed by identifying them according to the date and test number.

Exemplary "Step-By-Step" instructions for the programmed Review Utility Mode are as follows:

1. Repeatedly press the Menu key (10) until the Review display such as depicted in FIG. 7 appears.
2. Use Up and Down keys (24, 26) to select the correct date and test number for the relevant procedure desired and press the Enter key (28).
3. Use the Up or Down keys (24, 26) to review the test.

Clear Utility Mode:

Exemplary "Step-By-Step" instructions for the programmed Clear Utility Mode are as follows:

1. Repeatedly press the Menu key (10) until the Clear display such as depicted in FIG. 8 appears.
2. Press the Yes key (26) to erase all tests performed in the Procedure Mode.
3. Press the No key (24) to erase a specific test. Use the Up and Down keys (24, 26) to select a particular test.
4. Press the Menu key (10) to exit Report Preparation:

The system of the present invention contemplates a report writing software which may optionally be included in the aforementioned kit for a diagnostic device of the present invention. As noted above, the diagnostic device (100) is used to assist the medical practitioner (physician, clinician, technician) in recording and analyzing the collected data. The report writing software extracts this information and transduces it into a consistent format in which the medical practitioner can enter his notes and/or impressions, including, for example, additional aspects of the patient's physical or psychological presentation, such as mood, range of motion, limitations, etc. For example, when the examining medical practitioner prepares a report, he or she can review the downloaded and stored procedure readings and can then enter "Indications for Referral" or "Impressions". If a technician is preparing a test report, the "Indications for Referral" or "Impressions" fields can optionally be left blank so that the examining physician can fill in these fields.

The following is a non-exhaustive list of illustrative functions for the Report Writer Software contemplated by the present invention:

1. Downloading stored procedure readings from the device (100) to an external device, such as a local computer. Alternatively, the results may be imported, downloaded, copied or otherwise transferred to a remote location, such as a remote storage device or cloud-based database.
2. Preparing reports.
3. Saving a test report as an editable document (such as a Word file) with an allocated filename onto a physical storage device, such as an external hard drive, disk, or CD-ROM, or alternatively to the aforementioned cloud database.

In a preferred embodiment, the test report may include: subject detail (patient data); indication for referral, entered by examining physician; method; result; impressions entered by examining physician; the measured STC values of the test; and the average value of the thirty-six STC measurements.

To download the collected data and test, a small USB connector, such as a mini-USB connector (42) of a USB cable (40), may be connected to the USB port (5) of the device (100) and a larger standard USB connector, such as a type-C USB connector (46) of the USB cable (40), is connected to the USB port on the practitioner's computer or external hard-drive. Alternatively, as noted above, the connection between diagnostic device (100) and remote storage and/or analysis device, such as a local or networked computer or external hard-drive or cloud database, may be wireless, e.g., over a cellular network or short-range connection such as Bluetooth®.

An illustrative overall programmed procedure for downloading the stored procedure measurements from the device (100) is as follows:

1. Make sure that the device (100) is in Ready mode.
2. Double click or otherwise activate the Report writer software icon.
3. Connect the device 2 and the computer using the USB cable.
4. The device (100) will display the USB icon on its display (30).
5. On the computer, click on the "Download from Device" button.
6. The computer screen will display those procedures stored in the device (100).
7. To select a particular test to be downloaded, highlight the test.
8. Click on the Download button (24).
9. Repeat steps 7 & 8 to download each test.
10. After downloading the tests required, click on the Return To Main Menu button.
11. To select a particular test to be deleted, highlight the test and click on the Delete button.

Illustrative step-by step instructions for using the programmed procedure for preparing reports are as follows:

1. Click on the "New Report" button, which starts the preparation of a final Word report.
2. To delete a downloaded test from the device, select the test to be deleted and then click on "Delete the downloaded test".
3. To delete all the tests downloaded from the Epi-Scan, click on "Delete All".
4. After analyzing the recorded data by clicking on "Next»" the programmed procedure will start preparing the test in Word format.
5. Click on "«Back" to see previous screens or "Return to Main Menu" to go back to the "Choose Patient Test" Screen.
6. After analyzing the recorded data by clicking on "Next»>", the programmed procedure will automatically start preparing the test in the Word format.

To See the "Final Reports" Prepared in Word:

1. Click on "Open Prepared Report."
2. A "Device Report" Screen will appear.
3. A list of the prepared tests will appear in the list box.
4. Double click on the prepared final Word report desired.

Data Analysis:

Internal tests of function and calibration are performed automatically at the time of setup. However, the BioCheck function in the Procedure Mode provides a real-time test of the device (100) function while making measurements on active biological tissue, i.e. glabrous skin. Since BioCheck samples are made at sites, which are physically far from each other (palms of the hands, forehead), the values obtained also give some initial information about the dynamic range of regional differences in sudomotor function.

Following the Procedure montage, discussed below and illustrated in FIGS. 11-28, allows for the creation of a matrix set of discrete measurements, each corresponding to the sympathetic sudomotor levels at each particular location. Each individual measurement reveals an absolute selective tissue conductance (STC) value, which reflects a result, which is analogous or proportional to the expected sympathetic sudomotor activity level for the site being measured at a given time. In practice, however, more valuable information can be obtained if the individual (absolute) values are compared to other surrounding or distant values in a relative manner. This approach allows high or low values to be reviewed within the context of their spatial distribution over the whole area being tested. In such a situation, excessively high or low local values (referred to herein as "asymmetries") may be interpreted relative to their surrounding results.

Thus, in a preferred embodiment, the Procedure montages require comparison between one side of the body and the other. In any clinical, neurophysiologic or radiologic investigation of the human nervous system, the standards of practice are to answer the questions (a) where is the problem and (b) what is the problem. Humans, and indeed most animals, exhibit bilaterally symmetry. As such, all parts of the nervous system generally consist of paired structures, i.e., body areas that occur on either side of the midline, the first step in trying to localize an abnormality is to determine which side of the body has the problem. Therefore much of the analysis of data in sympathetic sudomotor assessment is based on the detection of asymmetries or differences between values measured on the left and right sides.

The values commonly obtained during sympathetic skin assessment can range widely between one part of the body and another. The main reason for this is that there are large differences in the relative density of sweat glands over different body regions. High Selective Tissue Conductance values are often found over the palms of the hands, axillae, groin, and soles of the feet, even in normal subjects.

In addition to differences between different body regions, there are also differences in sympathetic sudomotor level between subjects (patients). It is for reasons such as this that the most effective interpretation of sudomotor levels is to use the subject as his or her own control. This means that results are compared (a) between sides along horizontal lines and (b) between proximal and distal regions measured along vertical lines. Accordingly, the pre-programmed montages of the present invention are designed to incorporate at least 4 adjacent quadrants. By comparing across quadrants, the physician can identify asymmetrical reading(s) and correlate the location of such asymmetry with the degree of pain involved and thus the severity of any underlying injury, disease or disorder.

Pre-programmed Montages:

Exemplary pre-programmed Montage Procedures, along with the corresponding body parts and locations of the measurements, are shown in FIGS. 12-28. The typical 6×6 matrix, with 6 rows and 6 columns, common to these montages, and numbering of each measurement site is illustrated in FIG. 11. For example: R2C2 is reading of location Row 2, Column 2. R6C3 is reading of location Row 6, Column 3. However, as noted above, the present invention contemplates alternative square and rectangular matrices. The key is to divide the target area into quadrants and take an equivalent number of readings at mirrored locations within each quadrant so as to allow the subject to be his or her own control, i.e., wherein comparing results between sides along horizontal lines and between proximal and distal regions measured along vertical lines to identify asymmetries.

In addition to the pre-programmed montage procedures illustrated in FIGS. 12-28, the present invention contemplates a montage is not restricted to any body area. The linear method can be analyzed in blocks or using the linear gradient technique.

Although this pattern of Sympathetic Skin Assessment is included as an S type or Standardized montage, its design is different from those established in the previous seventeen montages S01 to S17. Instead, the present montage (S18) is based upon an extension of the linear gradient method, in which measurements are made sequentially along each of two parallel lines. Since, this specific pattern lends itself to being used to compare (or transpose) gradients in sympathetic sudomotor activity, it is also known as the Gradient Transposition montage, or more simply as the Gradient montage.

Data collection for this montage consists of the same three opening (BioCheck 1,2,3) and closing (BioCheck 4, 5, 6) system tests that are used in montages S01 to S17. However the active portion of the assessment process is based upon making two sets of sequential measurements, located along homologous lines over each side of the body. Each of the measurement sites is referred to by a letter designating the side (L or R) and a number (01, 02, 03, etc.), indicating the position of that site in the series.

The Gradient Montage is often used when the goal of the procedure is to detect differences in values obtained at (a) opposite sides of the body and (b) adjacent sites, along longer lines of measurement, such as assessing paraspinal regions or entire limbs. It can be used to measure along lines, which run distally or proximally as long as the start points are indicated on the test report and the locations of each pair of test sites are homologous.

To perform this type of test, the S18 Gradient montage is selected from the Procedure mode. After the Identification number has been entered, the usual BioCheck 1, 2, and 3 measurements are made. Depending on the region of the body to be tested, a series of twenty sequential measurements can be made, one electrode diameter apart, along the previously selected line, but always beginning on the LEFT side (L01 to L20-L20). As soon as the test site R01 appears on the screen, begin making measurements along the same type of line on the opposite (RIGHT) side and continue at test sites R01 to R20. Complete the procedure by performing BioCheck 4, 5, and 6 measurements.

TABLE 2

| | |
|---|---|
| R01 | L01 |
| R02 | L02 |
| R03 | L03 |
| R04 | L04 |
| R05 | L05 |
| R06 | L06 |
| R07 | L07 |
| R08 | L08 |
| R09 | L09 |
| R10 | L10 |
| R11 | L11 |
| R12 | L12 |
| R13 | L13 |
| R14 | L14 |
| R15 | L15 |
| R16 | L16 |

TABLE 2-continued

| | |
|---|---|
| R17 | L17 |
| R18 | L18 |
| R19 | L19 |
| R20 | L20 |

L—Left side
R—Right side

Thus, the present invention is well adapted to carry out the objects and attain the ends and advantages mentioned above as well as those inherent therein. While presently preferred embodiments have been described for purposes of this disclosure, numerous changes and modifications will be apparent to those in the art. Such changes and modifications are encompassed within this invention as defined by the claims.

INDUSTRIAL APPLICABILITY

As noted previously, there is a need in the art for the quantitative assessment of corporeal pain. The present invention addresses this need by providing an apparatus, system and method in which pain, can be evaluated and indexed to determine not only its presence and location but its severity, and thus the location and severity of any underlying disease, disorder or injury associated therewith. The quantitative pain scale and database developed in the course of the present invention finds utility not only in the diagnosis and treatment of any underlying or associated disorder, disease or injury but also in determining the appropriate drug and dosage regimen, in distinguishing organic pain from psychosomatic pain and legitimate pain patients from drug seekers and opiod addicts, and in comparing the efficacy of different pain medications.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

The invention has been illustrated by reference to specific examples and preferred embodiments. However, it should be understood that the invention is intended not to be limited by the foregoing description, but to be defined by the appended claims and their equivalents.

What is claimed:

1. A system for the objective measurement of the degree of sympathetic nerve dysfunction and thus the severity of an underlying injury, disease, or disorder present at one or more target sites in a subject, said system comprising:
   a. a sensor head that includes a concentric bipolar electrode assembly configured to contact the skin of a subject at one or more target sites, apply a low voltage electrical signal to said target site for a pre-determined period of time, and thereby measure an absolute selective tissue conductance (STC) value associated with each of said one or more target sites,
   b. a command module that contains the requisite power, circuitry, and communication components to enable the activation of said sensor head, application of said electrical signal, and recordation of said absolute STC value(s) measured thereby; and
   c. an algorithm maintained by said command module that converts the absolute STC value(s) measured by said sensor head at each of said target site(s) into a scaled output correlated to the degree of sympathetic nerve dysfunction,
   wherein said algorithm includes the steps of:
   (1) automatically comparing an absolute STC value obtained from a first target site to a reference STC value obtained from:
      i. one or more second target sites on said subject, wherein said one or more second target sites comprise mirrored and/or bilateral equivalent(s) of said first target site;
      ii. prior readings for said subject at said first target site;
      iii. a database of absolute and relative STC data obtained from pain and/or normal pain-free patients; or
      iv. a combination thereof
   (2) calculating a degree of difference between said absolute STC value and said reference STC value, and
   (3) converting the degree of difference calculated in step (2) to a scaled output that corresponds to severity of an underlying sympathetic nerve dysfunction.

2. The system of claim 1, wherein said electrical signal is a high frequency AC signal in the range of 1 to 100 kHz.

3. The system of claim 1, wherein said algorithm includes the step of comparing the absolute STC value measured at a first target site to an absolute STC value measured at a second target site that is the bilateral mirror of said first target site.

4. The system of claim 1, wherein said sensor head is physically separated from said command module and said command module communication component(s) is/are configured to send and receive wireless signals to and from said sensor head, further wherein said sensor head includes its own power supply, means to record measurements, and means to transmit recorded measurements to said command module.

5. The system of claim 4 wherein said means to record measurements comprises an integral or on-board memory chip or memory card.

6. The system of claim 4, wherein said command module comprises a smartphone, a tablet device or laptop, or a remote microprocessor.

7. The system of claim 1, wherein said command module comprises a hand-held device housing and said sensor head is configured for ready attachment to and detachment from said hand-held housing.

8. The system of claim 7, wherein the power components of said command module comprise one or more rechargeable batteries disposed within a compartment of said hand-held device housing.

9. The system of claim 7, wherein said hand-held device housing further comprises a liquid crystal display, onboard microprocessor, and onboard data storage means to allow for collected data to be temporarily stored, recalled, analyzed and displayed until it can be downloaded or uploaded to a remote system.

10. The system of claim 7, wherein said sensor head is configured for detachable mounting to said hand-held housing by means of a flexible coupling.

11. The system of claim 10, wherein said flexible coupling comprises an articulated, pivoting base, further wherein said base includes a curved or ball type surface that is pivotably received in a mating socket on a distal neck portion of said device housing.

12. The system of claim 7, wherein said sensor head is configured for detachable mounting to said hand-held housing by means of screw-in type mounting.

13. The system of claim 12, wherein said screw-in type mounting is provided with spring loaded contact pins that complete a measurement circuit.

14. The system of claim 1, wherein said sensor head further includes one or more additional biosensors for measuring one or more additional physiological parameters through contact with the skin at said one or more target site(s), further wherein said one or more additional biosensors are selected from the group consisting of:
   a. thermosensors and optical infrared scanners capable of assessing the heat and temperature of the subject's skin at said one or more target site(s);
   b. sweat-based glucose, lactate and theophylline biosensors that enable non-invasive transdermal scoring of analyte concentration in the muscle tissue proximate to said one or more target site(s);
   c. pulse-oximeters that allow for measurement of oxygen saturation levels and assess pre- and post-flow to one or more target site(s); and
   d. ultrasonic sensors and transducers that enable assessment of the viability and recovery of muscle tissue proximate to said one or more target site(s).

15. A kit for the objective measurement of the degree of sympathetic nerve dysfunction and thus the severity of any underlying injury, disease, or disorder present in a subject, said kit comprising:
   (a) the components of the system of claim 14, including a plurality of said sensor heads, each in separate sterile wrappings and configured for disposable, single-use;
   (b) a series of pre-programmed montages that automate measurement of absolute STC values at a plurality of a neighboring target sites associated with a particular injury and comparison of said absolute STC values to a reference point to identify the presence of one or more asymmetries that correlate to the severity of nerve dysfunction; and
   (c) report-writing software.

16. A method for objectively measuring the degree of sympathetic nerve dysfunction and thus the severity of an underlying injury, disease, or disorder present at one or more target sites in a subject, wherein said method comprises the following steps:
   (a) identify a local area of tissue to be analyzed;
   (b) divide said tissue area into four quadrants;
   (c) using the system of claim 1, apply a low voltage electrical signal via the entire active surface of the bipolar electrode assembly on said sensor head to a series of aligned target sites within a first quadrant for a pre-determined period of time and record absolute STC values for each target site;
   (d) repeat step (c) in the second, third, and fourth quadrant;
   (e) using the system algorithm, compare the absolute STC values for each target site and identify one or more sites of asymmetry;
   (f) using the system algorithm, further compare the absolute STC value obtained at said one or more sites of asymmetry to a reference STC value obtained from (a) a prior reading for said subject at said identical local area; (b) a database of STC data collected from pain and/or normal pain-free patients; or (c) a combination thereof; and
   (g) using said system algorithm, transduce the degree of difference between the absolute STC value at said one or more sites of asymmetry and the reference values in steps (e) and (f) to quantify the degree of sympathetic nerve dysfunction and thus the severity of an underlying nerve dysfunction located at said one or more sites of asymmetry within said local area of tissue.

17. The method of claim 16, wherein said subject is a non-human animal.

18. The method of claim 16, wherein said subject is a non-verbal human.

19. The method of claim 16, further comprising the step of monitoring changes in absolute STC values at said one or more sites of asymmetry over time, before, during, and after the application of a first prescribed therapeutic regimen to determine the efficacy of said first therapeutic regimen in treating the underlying sympathetic nerve dysfunction associated therewith.

20. The method of claim 16, further comprising the step of monitoring changes in absolute STC values at said one or more target sites of identified as exhibiting nerve dysfunction over time, before, during, and after the application of a second prescribed therapeutic regimen to determine the efficacy of said second therapeutic regimen relative to said first therapeutic regimen.

21. The method of claim 16, further comprising the step of using said system algorithm to: (a) analyze differences in unilateral STC to discriminate among, diagnose and treat transient ischemic attacks ("TIA"), reversible ischemic neurological deficits, and completed unilateral hemispheric stroke, or (b) analyze STC regional differences to discriminate among, diagnose and treat various forms of migraine, cluster, tension, and other headache types.

* * * * *